US006514956B1

(12) United States Patent
Chen et al.

(10) Patent No.: US 6,514,956 B1
(45) Date of Patent: Feb. 4, 2003

(54) STEROIDS, THEIR PREPARATION, PHARMACEUTICAL COMPOSITIONS THEREOF AND USES OF THE COMPOUNDS

(75) Inventors: Lianzhi Chen, Jiangsu (CN); Lin Zuo, Shanghai (CN); Mingwai Wang, San Diego, CA (US); Zhengyu Ye, Zhejiang (CN); Wenliung Chen, Shanghai (CN)

(73) Assignees: Shanghai Zhongxi Pharmaceutical Co., Ltd. (CN); Xianju Pharmaceutical Co., Ltd. (CN)

( * ) Notice: Subject to any disclaimer, the term of this patent is extended or adjusted under 35 U.S.C. 154(b) by 0 days.

(21) Appl. No.: 09/830,935
(22) PCT Filed: Aug. 31, 2000
(86) PCT No.: PCT/CN00/00255
§ 371 (c)(1),
(2), (4) Date: Aug. 1, 2001
(87) PCT Pub. No.: WO01/18026
PCT Pub. Date: Mar. 15, 2001

(30) Foreign Application Priority Data

Sep. 2, 1999 (CN) .......................... 99116829 A

(51) Int. Cl.[7] .......................... A61K 31/565; C07J 1/00; C07J 41/00; C07J 75/00
(52) U.S. Cl. .................. 514/177; 552/557; 552/582; 552/592; 552/598
(58) Field of Search ................ 514/177, 178; 552/592, 598

(56) References Cited

U.S. PATENT DOCUMENTS 4,634,695 A * 1/1987 Torelli et al. .............. 514/178
4,814,327 A * 3/1989 Ottow et al. ................ 260/397
5,272,140 A * 12/1993 Loozen ....................... 514/172

OTHER PUBLICATIONS

Zhao et al. (DN 115:270851, CAPLUS, abstract of Zhongguo Yaoke Daxue Xuebao (1991), 22(3), 133–6).*
Neff et al. (DN 109:93429, CAPLUS< abstract of DE 3621024).*
Ottow et al. (DN 104:207512, CAPLUS, abstract of Steroids (1984), 44(6), 519–30).*

* cited by examiner

*Primary Examiner*—Sabiha Qazi
(74) *Attorney, Agent, or Firm*—Pennie & Edmonds LLP

(57) ABSTRACT

The present invention concerns with steroid compounds of formula (I)

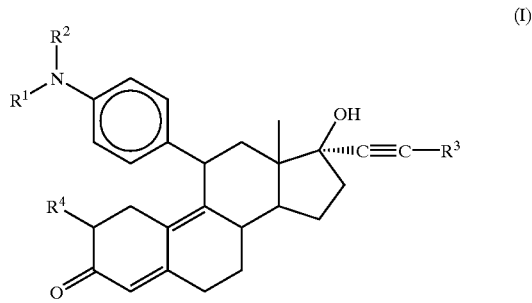

(I)

wherein $R^1$ is cyclohexyl or cycloheptyl, $R^2$ is hydrogen or $C_1$–$C_6$ alkyl, $R^3$ is hydrogen, $C_1$–$C_6$ alkyl or methylol, $R^4$ is hydrogen or hydroxymethylene and a pharmaceutically acceptable salt thereof. The invention also concerns with a method for preparation of the compounds, pharmaceutical compositions containing the compounds as its active component and use of the compounds and the pharmaceutical compositions in preparing medicines for treating diseases, e.g. those associated with progestin dependence.

25 Claims, No Drawings

STEROIDS, THEIR PREPARATION, PHARMACEUTICAL COMPOSITIONS THEREOF AND USES OF THE COMPOUNDS

FIELD OF THE INVENTION

This invention relates to steroid compounds and pharmaceutical acceptable salts thereof, a method for preparation thereof, pharmaceutical compositions containing the same as active component, and their use in the preparation of medicines for treating diseases associated with progestogen dependence and for fertility control, abortion or contraception and for anticancer use.

BACKGROUND OF THE INVENTION

Mifepristone (11β-[4-(N,N-dimethylamino)phenyl]-17α-(1-propinyl)-17β-hydroxy-4,9-estradiene -3-one) is a steroid compound which is disclosed in French Patent No. 2, 497, 807 to Rousell-Uclaf, published May 31, 1983. It is the first progesterone receptor antagonist put into clinical application and is a new type of anti-progestin. It binds to progesterone receptor and glucocorticoid receptor, having an affinity with progesterone receptor in rabbit endometrium five-fold higher than that of progesterone and thereby having strong anti-progesterone effect. It causes degeneration of pregnant villus tissue and decidual tissue, endogenous prostaglandin (PG) release, luteinizing hormone decrease, corpus luteum dissolution, and necrosis of embryo sac whose development depends on corpus luteum, leading to abortion. Therefore, it can be used as a non-surgical medicine for stopping early pregnancy. It can also be used, inter alia, in contraception and as an antineoplastic. (The Antiprogestin Steroid Ru486 and Human Fertility Control, 1985, New York: Plenum Press).

Onapristone (11β-[4-(N,N-dimethylamino)phenyl]-17α-hydroxy-17β-(3-hydroxypropyl)-13α-4,9-estradiene-3-one), is a steroid compound which is disclosed in German Patent No. 3, 321, 826 to Schering A G, published Dec. 20, 1984. It has a strong antiprogestin activity and can be used in abortion (American Journal of Obstetrics and Gyencology, 1987, 157:1065–1074), anticancer (Breast Cancer Research and Treatment, 1989, 14:275–288), etc. It was reported that onapristone had toxicity to human liver (European Journal of Cancer, 1999, 35(2): 214–218).

Lilopristone (11β-[4-(N,N-dimethylamino)phenyl]-17α-[3-hydroxy-1(Z)-propenyl]-17β-hydroxy-4,9-estradiene-3-one) is a steroid compound which is disclosed in German Patent No. 3, 347, 126 to Schering A G, published Jul. 11, 1985. It has a strong antiprogestin activity and can be used in abortion, contraception (American Journal of Obstetrics and Gyencology, 1987, 157:1065–1074), etc. It was reported that the clinical effect of lilopristone in stopping early pregnancy was only equivalent to that of mifepristone (Human Reproduction, 1994, 9(1): 57–63).

ZK112993 (11β-(4acetylphenyl)-17α-(1-propinyl)-17β-hydroxy-4,9-estradiene-3-one) is a steroid compound which is disclosed in German Patent No. 3, 504, 421 to Schering A G, published Aug. 7, 1986. It has a potent antiprogestin activity and can be used in, inter alia, anticancer (Anticancer Res., 1990, 10: 683–688).

In European Patent No. 321, 010 to Akzo N V, The Netherland published Jun. 21, 1989 are disclosed "11-arylsteroid compounds" having a strong antiprogestin activity.

OBJECT OF THE INVENTION

An object of the invention is to provide a class of steroid compounds of pharmaceutical value, especially having anti-progestin effect.

Another object of the invention is to provide a method for preparation of the steroid compounds.

Still another object of the invention is to provide pharmaceutical compositions for treating diseases associated with progestin dependence, and for fertility control, abortion or contraception and neoplasm control.

A further object of the invention is to provide use of said steroid compounds and pharmaceutical compositions in the preparation of medicines for treating diseases associated with progestin dependence, and for fertility control, abortion or contraception and neoplasm control.

DETAILED DESCRIPTION OF THE INVENTION

The steroid compounds of the present invention has the following general formula (I):

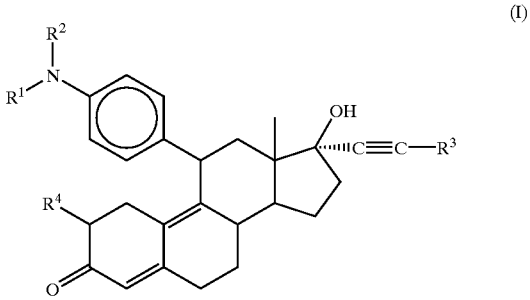

wherein $R^1$ is cyclohexyl or cycloheptyl, $R^2$ is hydrogen or $C_1$–$C_6$ alkyl, $R^3$ is hydrogen, $C_1$–$C_6$ alkyl or methylol, $R^4$ is hydrogen or hydroxymethylene (=CHOH).

The compounds of the present invention can be existed in the form of their salts. Also, due to multiple asymmetric carbon atoms contained therein, there may be many isomers of the compounds. These salts and isomers all fall within the scope of compounds of the present invention sought for protection.

The compounds of formula (I) of this invention are preferably those wherein $R^2$ is hydrogen or methyl and $R^3$ is methyl or methylol.

More preferred compounds of the invention include:
11β-[4-(N-methyl-N-cyclohexylamino)phenyl]-17α-(1-propinyl)-17β-hydroxy-4,9-estradiene-3-one,
11β-[4-(N-cyclohexylamino)phenyl]-17α-(1-propinyl)-17β-hydroxy-4,9-estradiene-3-one,
2-hydroxymethylene-11β-[4-(N-methyl-N-cyclohexylamino)phenyl]-17α-(1-propinyl)-17β-hydroxy-4,9-estradiene-3-one,
11β-[4-(N-methyl-N-cyclohexylamino)phenyl]-17α-(3-hydroxy-1-propinyl)-17β-hydroxy-4,9-estradiene-3-one,
11β-[4-(N-cyclohexylamino)phenyl]-17α-(3-hydroxy-1-propinyl)-17β-hydroxy-4,9-estradiene-3-one,
11β-[4-(N-methyl-N-cycloheptylamino)phenyl]-17α-(1-propinyl)-17β-hydroxy-4,9-estradiene-3-one,
11β-[4-(N-cycloheptylamino)phenyl]-17α-(1-propinyl)-17β-hydroxy-4,9-estradiene-3-one,
2-hydroxymethylene-11β-[4-(N-methyl-N-cycloheptylamino)phenyl]-17α-(1-propinyl)-17β-hydroxy-4,9-estradiene-3-one,
11β-[4-(N-methyl-N-cycloheptylamino)phenyl]-17α-(3-hydroxy-1-propinyl)-17β-hydroxy-4,9-estradiene-3-one,
11β-[4-(N-cycloheptylamino)phenyl]-17α-(3-hydroxy-1-propinyl)-17β-hydroxy-4,9-estradiene-3-one.

The preparation method of the present invention includes the following single- or multi-step procedures:
1. Method for the preparation of 11β-[4-(N-methyl-N-cyclohexylamino)phenyl]-17α-(1-propinyl)-17β-hydroxy-4,9-estradiene-3-one (VI) which includes the following steps:

(1) Preparation of Grignard Reagent (III)

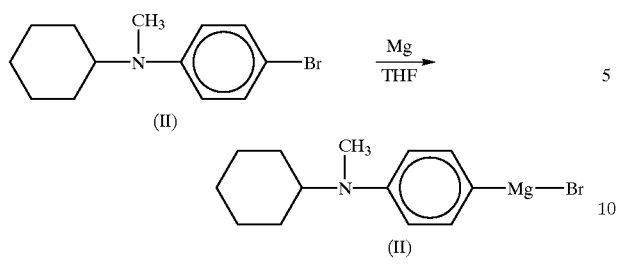

4-bromo-N-methyl-N-cyclohexylaniline (II) is reacted with magnesium in tetrahydrofuran (THF) to obtain Grignard reagent of formula (III).

(2) C$_{11}$ Additive Reaction

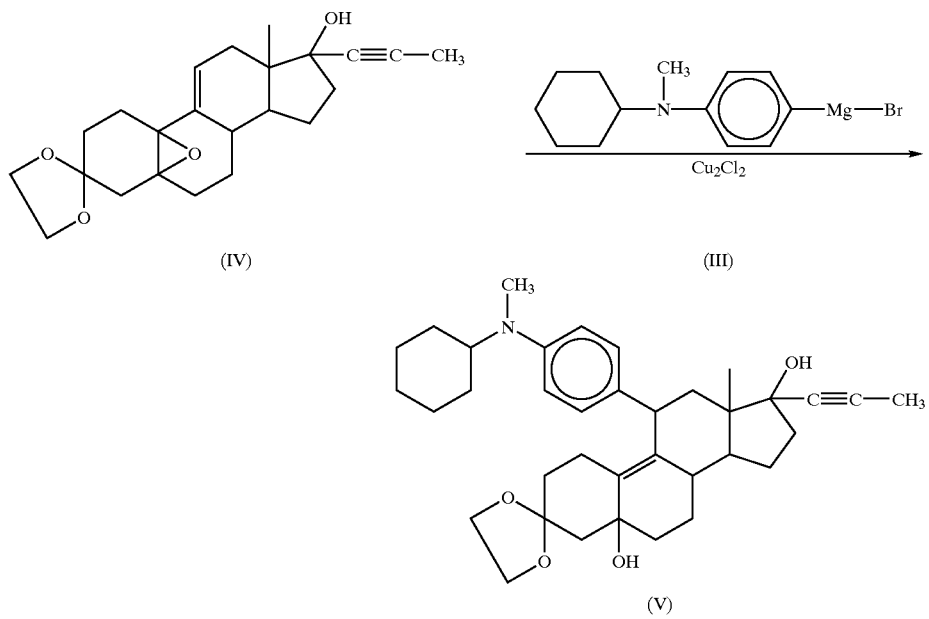

Compound of formula (IV) and the Grignard reagent of formula (III) prepared in step (1) are brought to an additive reaction to obtain compound of formula (V).

(3) Hydrolytic Reaction

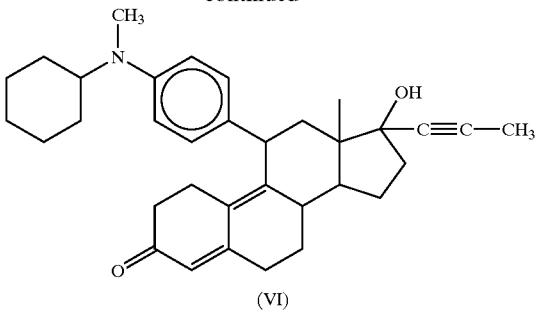

The compound of formula (V) prepared in step (2) is subjected to a Hydrolytic reaction to obtain compound of form (VI).

2. Method for preparation of 11β-[4-(N-cyclohexylamino)phenyl]-17α-(1-propinyl)-17β-hydroxy-4,9-estradiene-3-one (XI) which includes the following steps:

(1) Preparation of Grignard Reagent of Formula (IX)

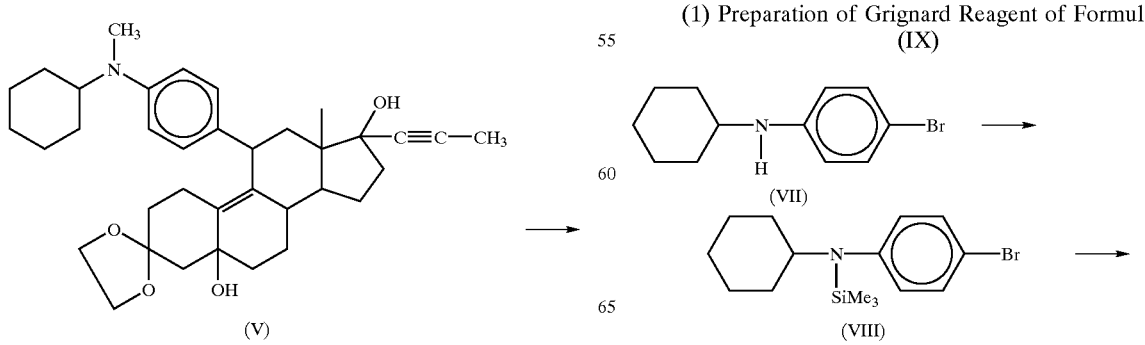

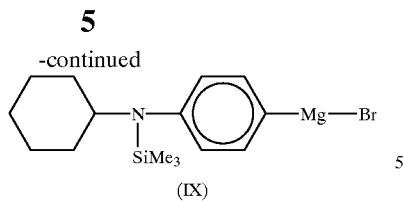

4-bromo-N-cyclohexylaniline (VII) is first protected by trimethylchlorosilane, then reacted with magnesium in THF to obtain Grignard reagent of formula (IX).

(2) C₁₁ Additive Reaction

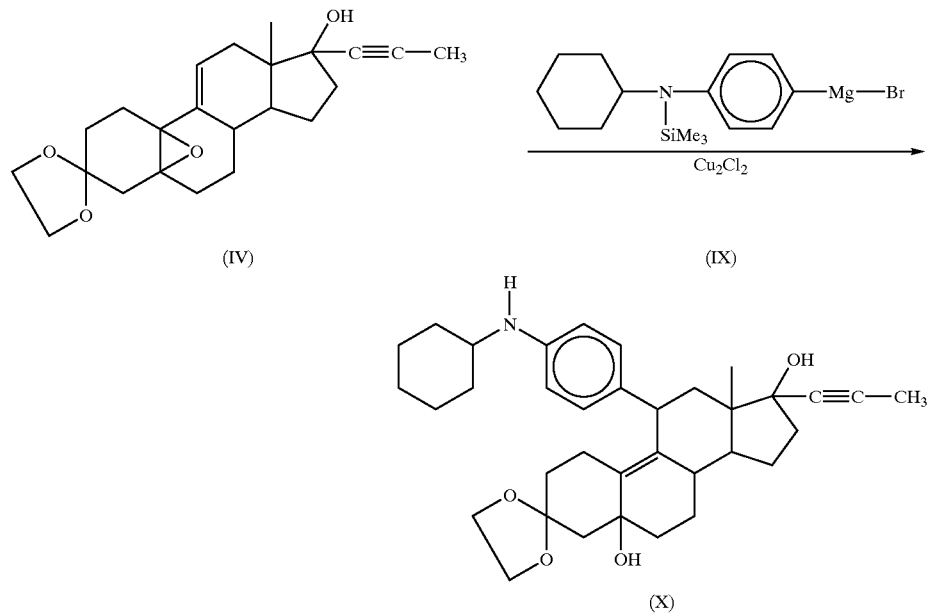

Compound of formula (IV) and the Grignard reagent of formula (IX) prepared in step (1) are brought to an additive reaction to obtain compound of formula (X).

(3) Hydrolytic Reaction

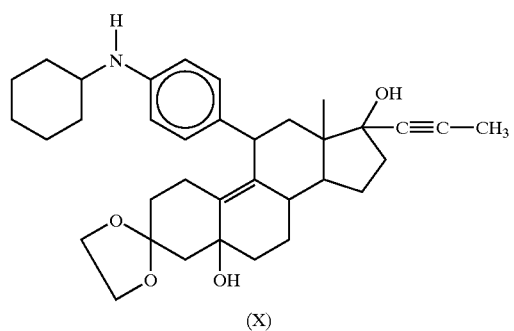

-continued

The compound of formula (X) prepared in step (2) is subjected to a hydrolytic reaction to obtain compound of formula (XI).

3. Method for preparation of 2-hydroxymethylene-11β-[4-(N-methyl-N-cyclohexylamino)phenyl]-17α-(1-propinyl)-17β-hydroxy4,9-estradiene-3-one (XII) which includes a formylation reaction as follows:

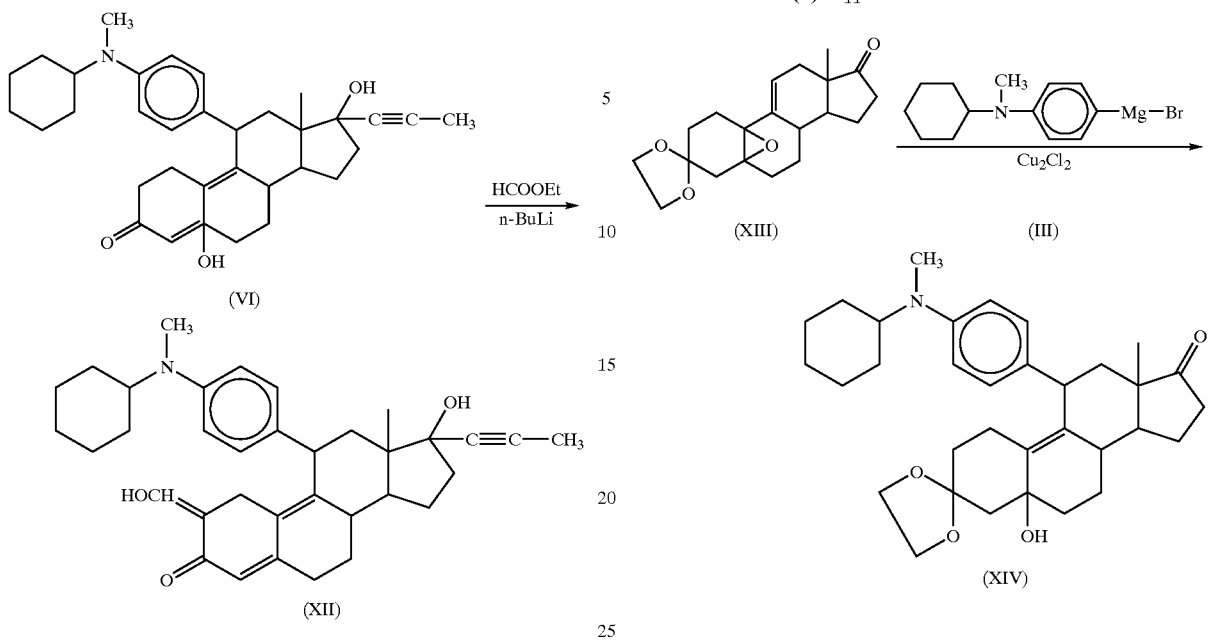

Compound of formula (VI) is subjected to a formylation reaction to obtain compound of formula (XII).

4. Method for preparation of 11β-[4-(N-methyl-N-cyclohexylamino)phenyl)]-17α-(3-hydroxy-1-propinyl)-17β-hydroxy-4,9-estradiene-3-one (XVII) which includes the following steps:

(1) $C_{11}$ Additive Reaction

Compound of formula (XIII) and the Grignard reagent of formula (III) prepared in step (1) according to claim 13 are brought to an additive reaction to obtain compound of formula (XIV).

(2) $C_{17}$ Additive Reaction

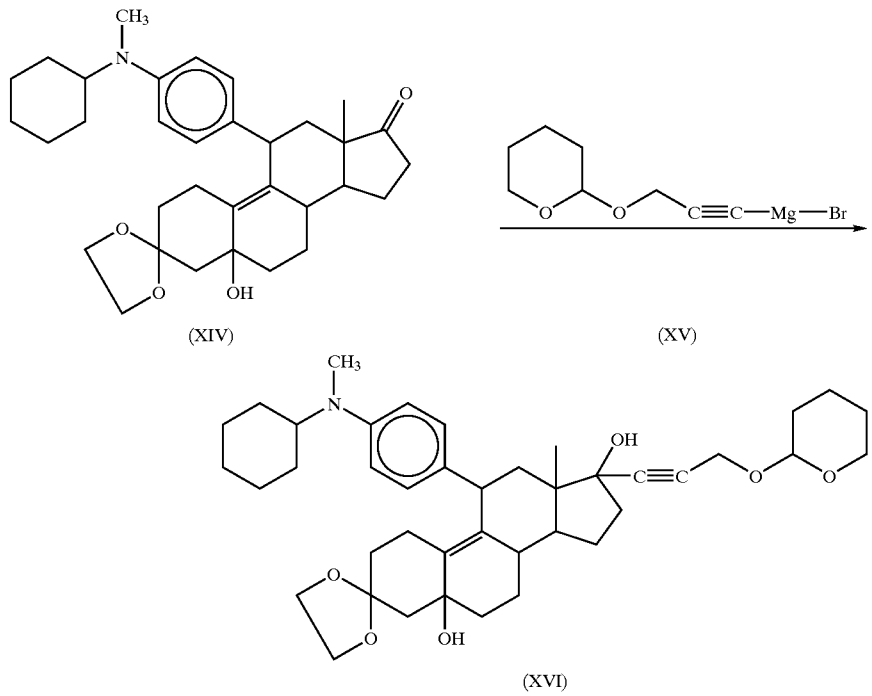

Compound of formula (XIV) prepared in step (1) and Grignard reagent of formula (XV) are brought to an additive reaction to obtain compound of formula (XVI).

(3) Hydrolytic Reaction

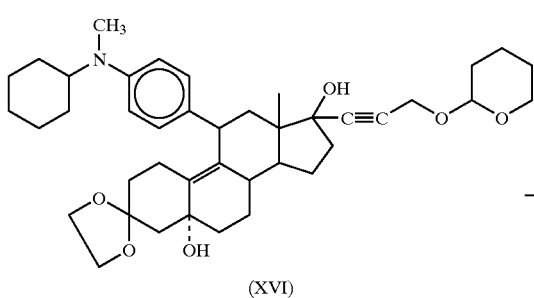

(XVI)

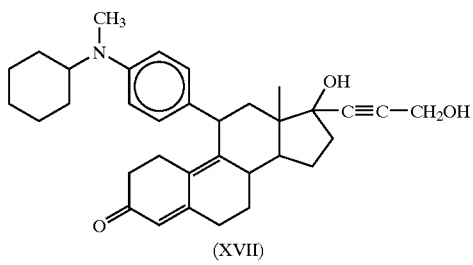

(XVII)

The compound of formula (XVI) prepared in step (2) is subjected to a hydrolytic reaction to obtain compound of formula (XVII).

5. Method for preparation of 11β-[4-(N-cyclohexylamino)phenyl]-17α-(3-hydroxy-1-propinyl)-17β-hydroxy-4,9-estradiene-3-one (XX) which includes the following steps:

(1) $C_{11}$ Additive Reaction

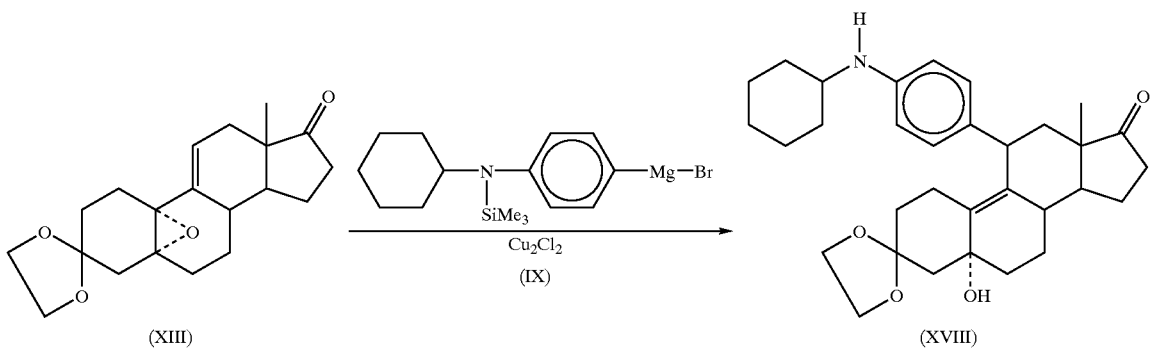

Compound of formula (XIII) and Grignard reagent of formula (IX) are brought to an additive reaction to obtain compound of formula (XVIII).

(2) $C_{17}$ Additive Reaction

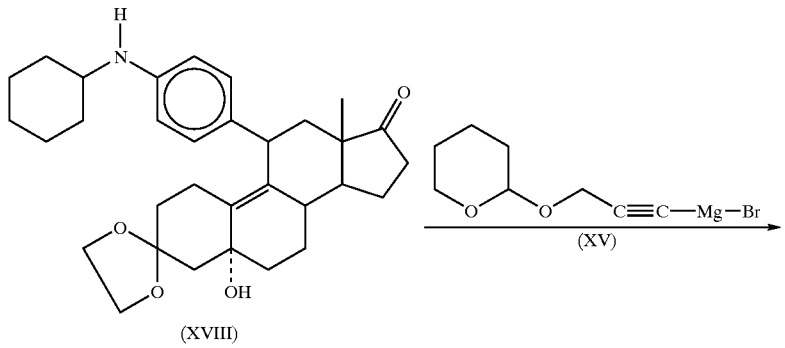

-continued

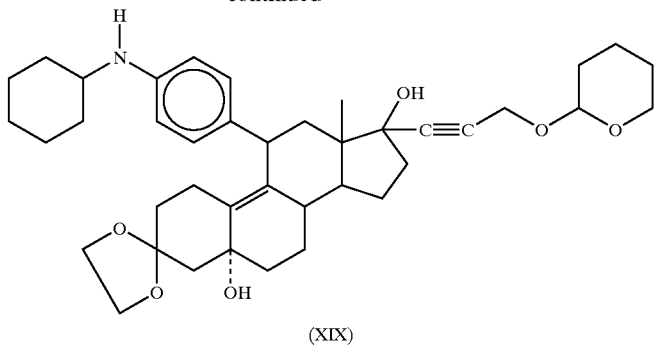

(XIX)

The compound of formula (XVIII) prepared in step (1) and Grignard reagent of formula (XV) are brought to an additive reaction to obtain compound of formula (XIX).

(3) Hydrolytic Reaction

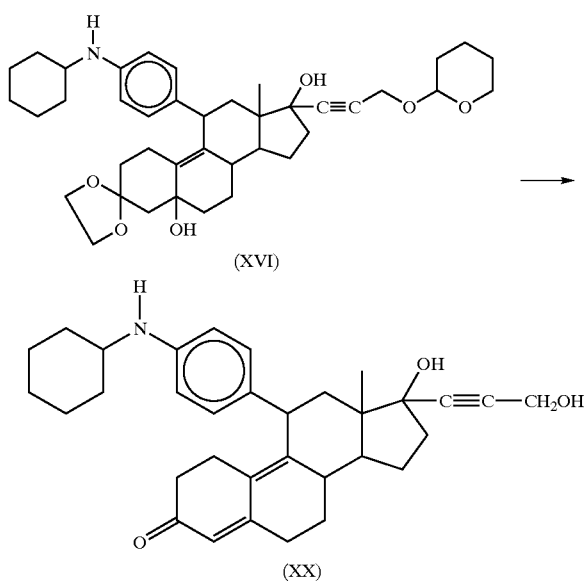

The compound of formula (XIX) prepared in step (2) is subjected to a hydrolytic reaction to obtain compound of formula (XX).

The compounds of the present invention can be combined with pharmaceutically acceptable carriers, pharmaceutically acceptable auxiliaries or other medicines to obtain pharmaceutical compositions for use in treating diseases associated with progestin dependence, controlling fertility, abortion or contraception, controlling neoplasm, etc., for example, use in treating mammary cancer, oophoroma, endometrial carcinoma, meningioma, hysteromyoma, endometriosis, premenstrual syndrome, and Cushing's Syndrome, and use in abortion and contraception, etc. The compounds of the invention, the pharmaceutical compositions containing them, and the use thereof in the preparation of medicines for treat diseases associated with progestin dependence all fall within the scope the present invention sought for protection.

The compounds of the present invention can be prepared as their pharmaceutically acceptable salts with proper acids. The proper acids which can be used to produce the pharmaceutically acceptable salts are, for example, inorganic acids, e.g. hydrochloric acid, hydrobromic acid, nitric acid, sulfuric acid, phosphoric acid, etc; organic acids, e.g. formic acid, acetic acid, propanoic acid, benzoic acid, maleic acid, fumaric acid, succinic acid, tartaric acid, citric acid, etc; alkyl sulfonic acid, e.g. methyl sulfonic acid, ethyl sulfonic acid, etc; aryl sulfonic acid, e.g. benzene sulfonic acid, p-toluene sulfonic acid, etc.

Pharmaceutical compositions containing the compounds of the invention comprise pharmaceutically effective amount of the compounds of the invention and pharmaceutically acceptable carriers or auxiliaries or other medicines that are compatible with the compounds of the present invention.

The pharmaceutically acceptable carriers and auxiliaries for the compounds of the invention or in the pharmaceutical compositions containing the same may be starch and derivatives thereof, cellulose and derivatives thereof, cyclodextrin and derivatives thereof, high molecular polymers, organic acids and their salts and esters, inorganic compounds such as inorganic calcium salts and oxides, higher alcohols, phospholipids, saccharides and other suitable materials.

The compounds of the invention and the pharmaceutical compositions containing the same may be in solid dosage forms such as tablets, capsules, drop pills, granules and suppositories, or may be in the form of liquid formulations such as injection, suspension, emulsion and solution, or may be in the form for percutaneous administration and also dosage forms having special effects such as sustained release, controlled release, targeted release and pulsed release.

EFFECTS OF THE INVENTION

The present inventors found that the compounds of the invention have good effects in treating diseases associated with progestin dependence and in fertility control, abortion or contraception and neoplasm control. Compared with mifepristone, the compounds of the present invention have better effects in killing tumor cells, inhibiting MNU-induced rat mammary cancer, and stopping early pregnancy and inhibiting implanation in rat.

The following preparation examples and working examples are intended to further demonstrate the invention. It is to be understood that these preparation examples and working examples serve to illustrate the invention only but not to limit the invention.

PREPARATION EXAMPLES

Preparation Example 1

Preparation of 4-bromo-N-methyl-N-cyclohexyl aniline (II)

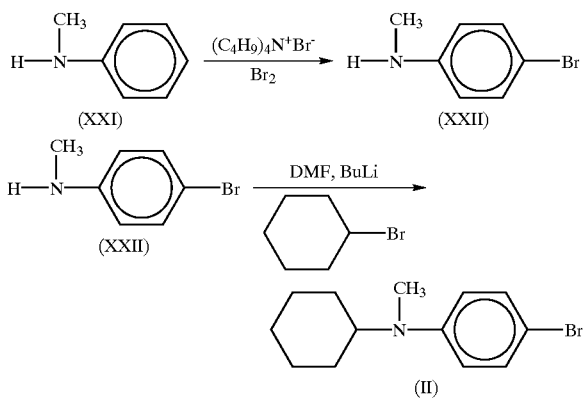

(1) Preparation of 4bromo-N-methylaniline (XXII)

10.7 g N-methylaniline (XXI), 32.1 g tetrabutylammonium bromide [$(C_4H_9)_4N^+Br^{31}$] and 100 ml methylene chloride ($CH_2Cl_2$) were placed in a three-necked flask and cooled down to 0° C. with iced saline. 15.8 g bromine ($Br_2$) was dropped slowly with stirring and was stirred for 4 hours while maintaining at 0° C. The temperature was allowed to raise to room temperature and saturated sodium carbonate solution was dropped slowly till evolution of carbon dioxide is ceased. Water layer was separated and extracted with methylene chloride for three times. The organic layers were combined and dried over anhydrous sodium sulfate. Methylene chloride was evaporated to yield 26 g 4-bromo-N-methylaniline (XXII).

(2) Preparation of 4bromo-N-methyl-N-cyclohexyl aniline (II)

26 g 4-bromo-N-methylaniline (XXI) and 100 ml anhydrous N,N-dimethyl formamide ($HCONEt_2$) were plced into a four-necked flask and cooled down to 0° C. under nitrogen. 40 ml of 2.5 M n-butyl lithium (n-BuLi) solution in n-hexane was dropped with stirring and stirred for 2 hours while maintaining at 0° C. N-hexane and n-butane were evaporated and 16.2 g bromo-cyclohexane was added and stirred under reflux for 8 hours. After cooling, lithium bromide was filtered off and N,N-dimethyl formamide recovered. The residue was recrystallized twice from 95% ethanol to yield 16 g 4bromo-N-methyl-N-cyclohexyl aniline (II).

IR (KBr) $cm^{-1}$: 2938, 2851 ($CH_3$, $CH_2$), 1449, 1358 ($CH_3$, $CH_2$), 1585, 1495.9 (benzene backbone), 1316.8 (C—N), 806.1 (benzene ring 1, 4 substitution).

$^1$HNMR ($CDCl_3$) δ ppm: 1.12–1.82 (10 H, m, cyclohexane), 2.73 (3H, S, N—$CH_3$), 6.62–7.27 (4H, ArH).

Preparation Example 2

Preparation of 4bromo-N-methyl-N-cycloheptyl aniline (XIII)

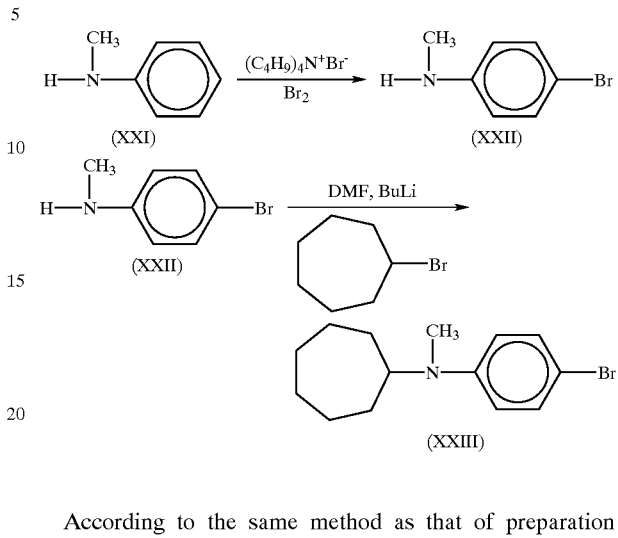

According to the same method as that of preparation example 1 replacing bromo-cyclohexane with bromo-cycloheptane, the title compound, 4bromo-N-methyl-N-cycloheptyl aniline (XXIII) was obtained.

IR (KBr) $cm^{-1}$: 2930, 2846 ($CH_3$, $CH_2$), 1455, 1360 ($CH_3$, $CH_2$), 1581, 1497 (benzene backbone), 1319 (C—N), 810 (benzene ring 1, 4 substitution).

$^1$H NMR ($CDCl_3$) δ ppm: 1.10–1.87 (12 H, m, cycloheptyl), 2.82 (3H, S, N—$CH_3$), 6.58–7.30 (4H, ArH).

Preparation Example 3

Preparation of 4-bromo-N-cycloheptyl aniline (XXV)

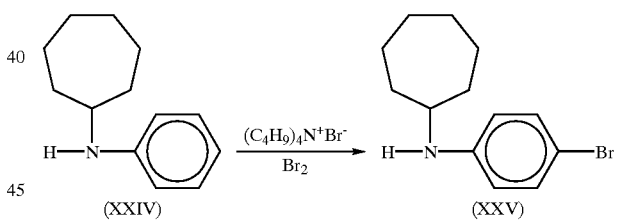

18.9 g N-cycloheptyl aniline (XXIV) (CA registration number [61142-86-7], see Synthesis, 1991, 11:1043–1045 for its preparation), 32.1 g tetrabutylammonium bromide [$(C_4H_9)_4N^+Br^-$] and 100 ml methylene chloride ($CH_2Cl_2$) were placed into a three-necked flask and cooled down to 0° C. with iced saline. 15.8 g bromine ($Br_2$) was dropped slowly with stirring and was stirred for 4 hours while maintaining at 0° C. The temperature was allowed to raise to room temperature and saturated sodium carbonate solution was dropped slowly till evolution of carbon dioxide ceased. Water layer was separated and extracted with methylene chloride for three times. The organic layers were combined and the solvent evaporated. The residue was recrystalized from 95% ethanol for two times to yield 21.4 g 4bromo-N-cycloheptyl aniline (XXV).

IR (KBr) $cm^{-1}$: 3400 (NH), 2931, 2842 ($CH_2$), 1460 ($CH_2$), 1585, 1500 (benzene backbone), 1250 (C—N), 809 (benzene ring 1, 4 substitution).

$^1$H NMR ($CDCl_3$) δ ppm: 1.08–1.90 (12 H, m, cycloheptyl), 6.60–7.29 (4H, ArH).

EXAMPLES

The method for preparation of the steroid compounds of the present invention is illustrated as follows:

Example 1

Preparation of 11β-[4-(N-methyl-N-cyclohexylamino)phenyl]-17α-(1-propinyl)-17β-hydroxy-4,9-estradiene-3-one (VI)

(1) Preparation of 4-(N-methyl-N-cyclohexylamino)phenyl-magnesium bromide (III)

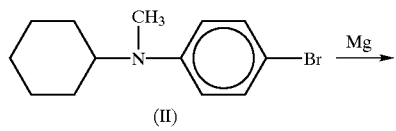

(II)

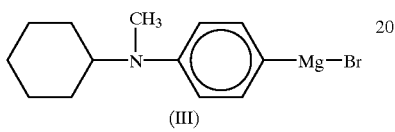

(III)

1.4 g magnesium (Mg) and 10 ml anhydrous tetrahydrofuran (THF), (with or without a small amount of iodine added) were placed into a four-necked flask. At about 50° C., 10.86 g 4-bromo-N-methyl-cyclohexyl aniline (II) (CA registration number [88799-11-5], see preparation example 1 for its preparation) dissolved in 24 ml anhydrous tetrahydrofuran was added dropwise. After completion of addition, stirring was continued for 1 hour while maintaining the temperature to yield 4-(N-methyl-N-cyclohexylamino) phenylmagnesium bromide (III) in anhydrous tetrahydrofuran (for use in the next step of additive reaction).

(2) Preparation of 3,3-ethylenedioxy-5α,17β-dihydroxy-11β-[4-(N-methyl-N-clohexylamino)phenyl]-17α-(1-propinyl)-9(10)-estrene(V)

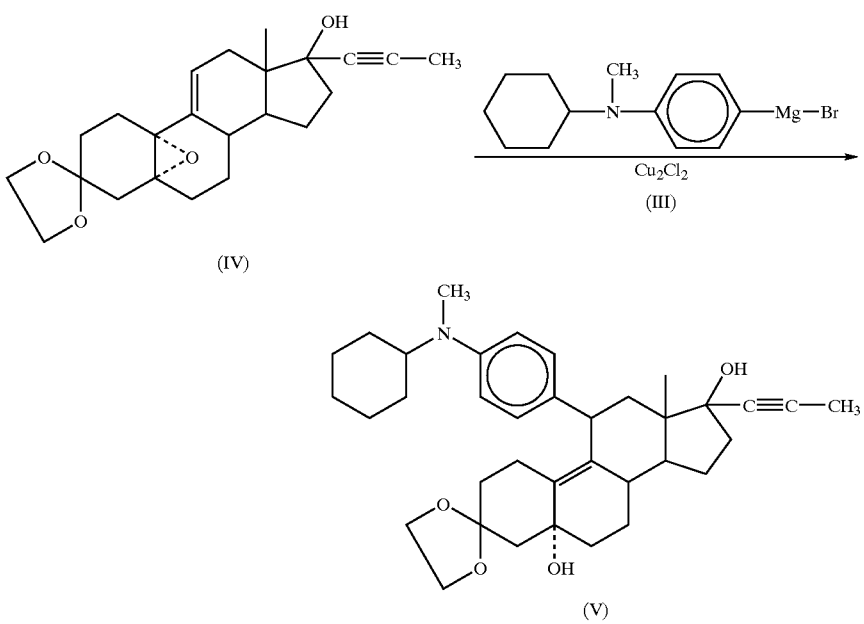

5 g 3,3-ethylenedioxy-5,10-epoxy-17α-(1-propinyl)-17β-hydroxy-9(11)-estrene (IV) (CA registration number [84371-57-3], see U.S. Pat. No. 4,386,085 for its preparation), 29.1 ml anhydrous tetrahydrofuran (THF) and 0.1 g cuprous chloride (Cu₂Cl₂) were placed into a four-necked flask. 4N-methyl-N-cyclohexylamino) phenylmagnesium bromide (III) in tetrahydrofuran was added dropwise while maintaining the temperature below 5° C. After completion of addition, the reaction was allowed to continue for 5 hours while maintaining the temperature. Upon completion of the reaction, the reaction was poured into aqueous saturated ammonium chloride solution. Water layer was separated. The organic layer washed with saturated ammonium chloride solution and the water layer extracted with ethyl acetate for several times. The combined organic layers were washed with saturated sodium chloride aqueous solution, dried over anhydrous sodium sulfate, concentrated under reduced pressure and separated on silica gel column using cyclohexane:acetone=(5:1) as developping agent to yield 6 g 3,3-ethylenedioxy-5α,17β-dihydroxy-11β-[4-(N-methyl-N-cyclohexylamino)phenyl]-17α-(1-propinyl)-9(10)-estrene (V) as a solid.

IR (KBr) cm$^{-1}$: 3515 ($C_5$—OH, $C_{17}$—OH), 1612, 1515 (benzene backbone), 819 (ArH).

$^1$H NMR (CDCl$_3$) δ ppm: 0.47 (3H, S, $C_{13}$—CH$_3$), 1.88 (3H, S, C≡C—CH$_3$), 2.72(3H, S, N—CH$_3$), 6.65–7.03 (4H, ArH).

(3) Preparation of 11β-[4-(N-methyl-N-cyclohexylamino)phenyl]-17α-(1-propinyl)-17β-hydroxy-4,9-estradiene-3-one (VI)

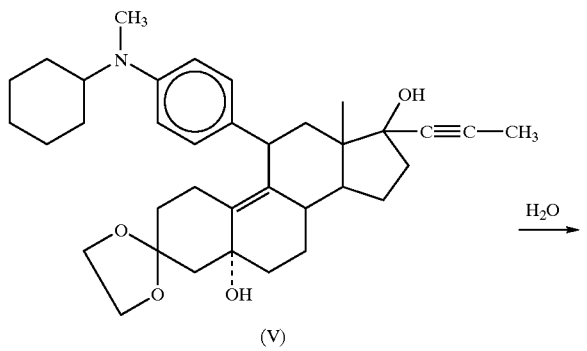

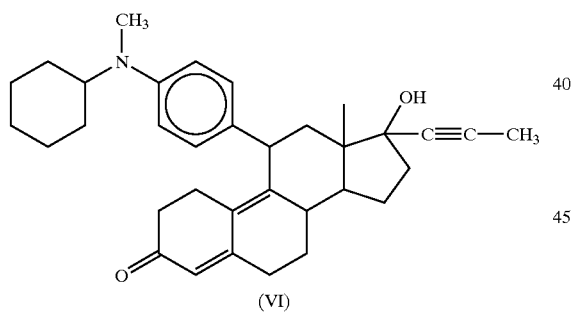

2.5 g para-toluenesulfonic acid (PTS) and 5 g 3,3-ethylenedioxy-5α,17β-dihydroxy-11β-[4-(N-methyl-N-cyclohexylamino)phenyl]-17α-(1- propinyl)-9(10)-estrene (V) were dissolved in 50 ml 90% ethanol (v/v). After reacting at 5° C.–40° C. for 3 hours with stirring, the reaction solution was poured into diluted sodium hydroxide aqueous solution. The precipitated solid was filtered under suction and washed with water to neutral. The filter cake was dissolved in 50 ml ethyl acetate and washed with saturated sodium chloride aqueous solution. The water layer was separated. Part of the solvent was removed by evaporation to precipitate a solid which was filtered under suction and dried to yield 3 g 11β-[4-(N-methyl-N-cyclohexylamino)phenyl]-17α-(1-propinyl)-17β-hydroxy-4,9-estradiene-3-one (VI) as a pale yellow solid.

IR (KBr) cm$^{-1}$: 3447 ($C_{17}$—OH), 1655 (unsaturated ketone), 1607, 1513 (benzene backbone), 865, 819(ArH).

$^1$H NMR (CDCl$_3$) δ ppm: 0.56 (3H, S, $C_{13}$—CH$_{13}$), 1.89 (3H, S, —C≡C—CH$_3$), 2.74 (3H, S, N—CH$_3$), 4.34 (1H, S, $C_{11}$—H), 5.75(1H, S, $C_4$—H), 6.68–6.99 (4H, ArH).

Example 2

Preparation of 11β-[4-(N-cyclohexylamino)phenyl]-17α-(1-propinyl)-17β-hydroxy-4,9-estradiene-3-one (XI)

(1) Preparation of 4-(N-cyclohexyl-N-trimethylsilylamino)phenyl magnesium bromide (IX)

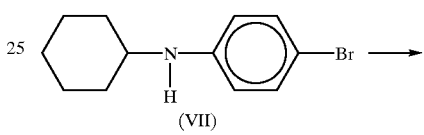

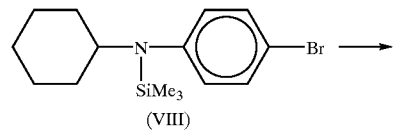

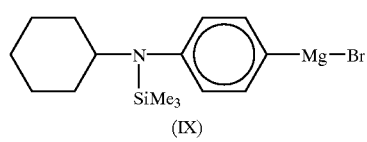

9 g 4-bromo-N-cyclohexylaniline (VII) (CA registration number [113388-04-8], see Synthetic Communications, 1986, 16(13): 1641–1645 for its preparation) was placed into a four-necked flask and 15 ml (1.5 mol/L) n-BuLi solution in n-hexane. The mixture was stirred for 30 min at room temperature. Then 8 g trimethylsilyl chloride (Me$_3$SiCl) was added and the mixture was stirred for 1 hour. Solvent and excessive Me$_3$SiCl was evaporated under reduced to yield 4-bromo-N-cyclohexyl-N-trimethylsilylaniline) (VIII) which was formulated into a solution with 7.5 ml anhydrous tetrahydrofuran for further use.

1.3 g magnesium was placed into a four-necked flask and a small amount of the above solution was added dropwise and slowly at 40° C. After completion of addition, the temperature was kept for 1 hour to yield a solution of 4-(N-cyclohexyl-N-trimethylsilylamino)phenylmagnesium bromide (IX) in tetrahydrofuran for further use.

(2) Preparation of 3,3-ethylenedioxy-5α,17β-dihydroxy-11β-[4-(N-clohexylamino)phenyl]-17α-(1-propinyl)-9(10)-estrene(X)

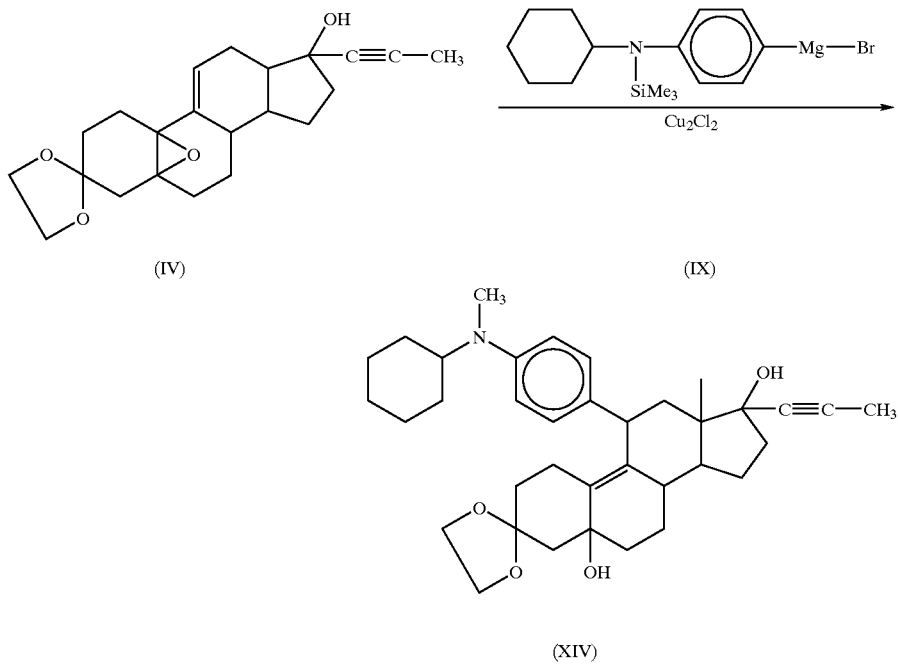

5 g 3,3-ethylenedioxy-5,10-epoxy-17α-(1-propinyl)17β-hydroxy-9(11)-estrene (IV) was placed into a four-necked flask and 10 ml anhydrous tetrahydrofuran and a catalytic amount of cuprous chloride (Cu$_2$Cl$_2$) added. Then solution of 4-(N-cyclohexyl-N-trimethylsilylamino)phenyl magnesium bromide (IX) in tetrahydrofuran was added dropwise and slowly while controlling the temperature below 5° C. After completion of addition, the mixture was allowed to react for 2 hours at room temperature and to stand overnight. Saturated ammonium chloride aqueous solution was added and the tetrahydrofuran layer separated which was washed with saturated ammonium chloride solution. The solution in tetrahydrofuran was washed with saturated saline and dried over anhydrous sodium sulfate. Evaporation of tetrahydrofuran under reduced pressure yielded a residual which was chromatographed on silica gel column using cyclohexane:acetone (5:1) as developing agent to yield 3 g 3,3-ethylenedioxy-5α,17β-dihydroxy-11β-[4-(N-cyclohexylamino)phenyl]-17α-(1-propinyl)-9(10)-estrene (X).

IR (KBr) cm$^{-1}$: 3420 (C$_5$, C$_{17}$—H), 1610, 1510 (benzene backbone), 840, 808 (ArH).

$^1$H NMR (CDCl$_3$) δ ppm: 0.52(3H, S, C$_{13}$—CH$_3$), 2.72 (3H, S, N—CH$_3$), 3.92(4H, m, —O—CH$_2$CH$_2$—O—), 4.24 (1H, m, C$_{11}$—H), 6.65–7.00 (4H, ArH).

(3) Preparation of 11β-[4-(N-cyclohexylamino)phenyl]-17α-(1-propinyl)-17β-hydroxy-4,9-estradiene-3-one (XI)

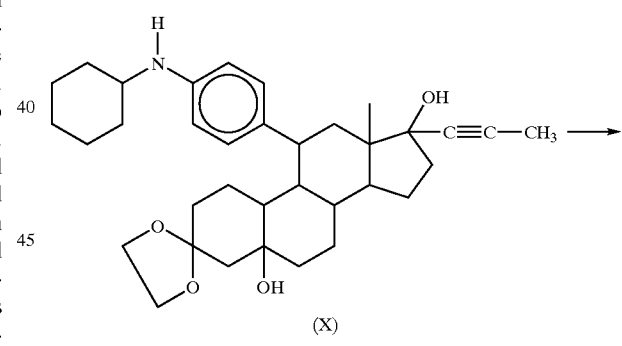

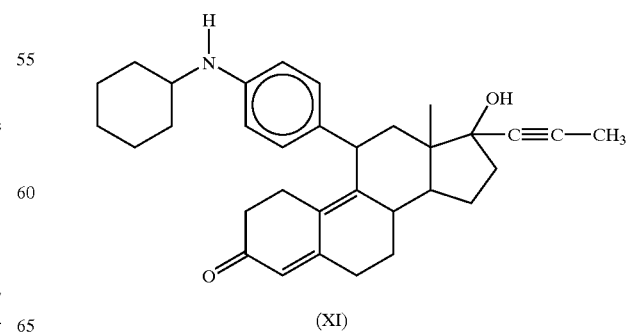

1.5 g 3,3-ethylenedioxy-5,17β-dihydroxy-11β-[4-(N-cyclohexylamino)phenyl]-17α-(1-propinyl)-9(10)-estrene (X) and 0.75 g para-toluenesulfonic acid (PTS) were dissolved in 15 ml 90% ethanol (v/v). The mixture was stirred for 2 hours while controlling the temperature at 40° C.–50° C. After completion of the reaction, the reactant was poured into diluted sodium hydroxide aqueous solution, extracted with dichloroethane, washed with water to neutrality, and dried over anhydrous sodium sulfate. Evaporation of the solvent and chromatography on silica gel column using cyclohexane:ethyl acetate (5:1) as developing agent yielded 0.9 g 11β-[4-(N-cyclohexylamino)phenyl]-17α-(1-propinyl)-17β-hydroxy-4,9-estradiene-3-one (XI).

IR (KBr) cm$^{-1}$: 3400 ($C_{17}$—OH), 1658 (unsaturated ketone), 1613, 1514 (benzene backbone), 865, 810(ArH).

$^1$H NMR (CDCl$_3$) δ ppm: 0.50(3H, S, $C_{13}$—CH$_3$), 1.76 (3H, S, —C≡C—CH$_3$), 4.32(1H, S, $C_{11}$C—H), 5.75(1H, S, $C_4$—H), 6.9–7.10 (4H, ArH).

Example 3

Preparation of 2-hydroxymethylene-11β-[4-(N-methyl-N-cyclohexylamino)phenyl]-17α-(1-propinyl)-17β-hydroxy-4,9-estradiene-3-one (XII)

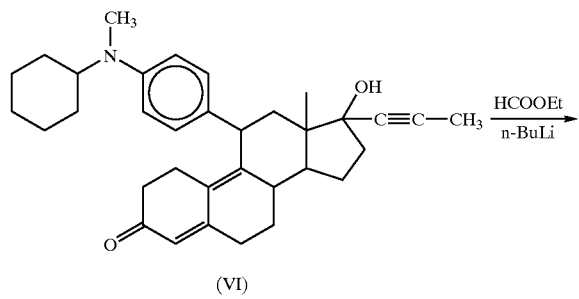

(VI)

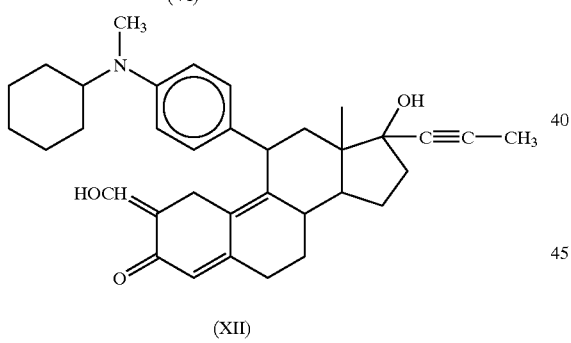

(XII)

4 g 11β-[4-(N-methyl-N-cyclohexylamino)phenyl]-17α-(1-propinyl)-17β-hydroxy-4,9-estradiene-3-one (VI) was dissolved in 18 ml anhydrous tetrahydrofuran (THF) and 13 ml (1.5 mol/L) n-butyl lithium (n-BuLi) solution in cyclohexane. The mixture was allowed to react for 30 min and 1.2 g anhydrous ethyl formate (HCOOEt) and warmed under reflux for 3 hours. Tetrahydrofuran was evaporated and water added. Extraction with ethyl acetate and chromatography on silica gel column using cyclohexane:ethyl acetate (5:1) as developing agent yielded 2 g 2-hydroxymethylene-11β-[4-(N-methyl-N-cyclohexylamino)phenyl]-17α-(1-propinyl)-17β-hydroxy-4,9-estradiene-3-one (XII).

IR (KBr) cm$^{-1}$: 3400 ($C_{17}$—OH, =C—OH), 1640 (unsaturated ketone), 1610, 1510 (benzene backbone), 865, 810 (ArH).

$^1$H NMR (CDCl$_3$) δ ppm: 1.01(3H, S, $C_{13}$—CH$_3$), 1.87 (3H, S, C≡C—CH$_3$), 2.75(3H, S, N—CH$_3$), 6.65–6.95 (4H, ArH).

Example 4

Preparation of 11β-[4-(N-methyl-N-cyclohexylamino)phenyl]-17α-(3-hydroxy-1-propinyl)-17β-hydroxy-4,9-estradiene-3-one (XVII)

(1) Preparation of 3,3-ethylenedioxy-5α-hydroxy-11β-[4-(N-methyl-N-cyclohexylamino)phenyl]-9(10)-estrene-17-one (XIV)

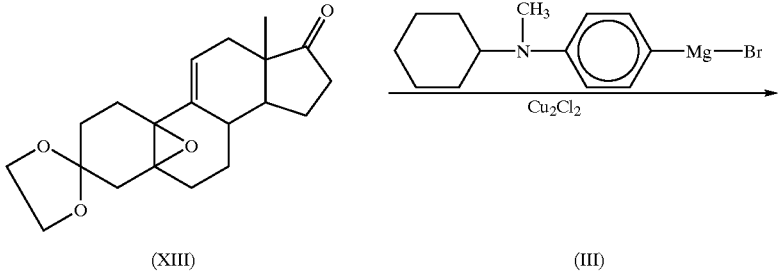

(XIII)  (III)

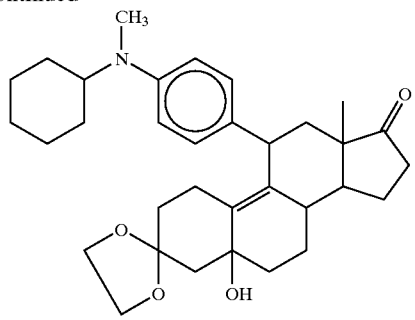

(XIV)

3.3 g 3,3-ethylenedioxy-5,10-epoxy-9(11)-estrene-17-one (XIII) (CA registration number [39931-87-8], see Transaction of China Pharmaceutical University, 1991, 22(3):133–136) for its preparation) was dissolved in 10 ml anhydrous tetrahydrofuran and a catalytic amount of cuprous chloride ($CU_2Cl_2$) was added. 0.04 mol 4-(N-methyl-N-cyclohexylamino)phenyl magnesium bromide (III) in tetrahydrofuran was added dropwise, while controlling the temperature below 0° C. After completion of addition, the mixture was allowed to react for 4 hours, added into saturated ammonium chloride solution, extracted with ethyl acetate, dried over anhydrous sodium sulfate, and chromatographed on silica gel column to yield 1.6 g 3,3-ethylenedioxy-5α-hydroxy-11β-[4-(N-methyl-N-cyclohexylamino)phenyl]-9(10)-estrene-17-one (XIV).

IR (KBr) cm$^{-1}$: 3420 ($C_5$—OH), 1730 ($C_{17}$ ketone), 1610, 1510 (benzene backbone), 808(ArH).

$^1$H NMR (CDCl$_3$) δ ppm: 0.52(3H, S, $C_{13}$—CH$_3$), 2.72 (3H, S, N—CH$_3$), 3.92(4H, m,—O—CH$_2$CH$_2$—O—), 6.56–7.00(4H, Ar—H).

(2) Preparation of 3,3-ethylenedioxy-5α,17β-dihydroxy-11β-[4-(N-methyl-N-cyclohexylamino)phenyl]-17α-[3-(2'-tetrahydropyranyloxy)-1-propinyl]-9(10)-estrene(XVI)

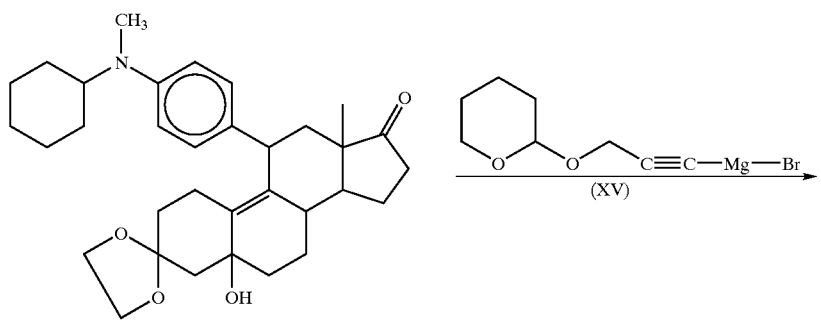

(XIV)

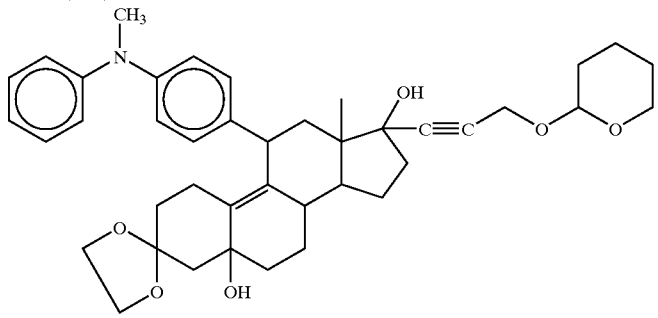

(XVI)

2.0 g 3,3-ethylenedioxy-5α-hydroxy-11β-[4-(N-methyl-N-cyclohexylamino)phenyl]-9(10)-estrene-17-one (XIV) dissolved in 14 ml anhydrous tetrahydrofuran (THF) was added dropwise into 36 ml of a 0.6 ml/l solution of 3-(2'-tetrahydropyranyloxy)-1-propinyl magnesium bromide (XV) (CA registration number is [51480-24-1], see Organic Syntheses, 1981, 60:81–87 for tis perparation) in tetrahydrofuran at 25° C. After completion of addition, the mixture was allowed to react for 2 hours, poured into saturated ammonium chloride solution, extracted with ethyl acetate, dried over anhydrous sodium sulfate and chromatographed on silica gel column to yield 1.8 g 3,3-ethylenedioxy-5α,17β-dihydroxy-11β-[4-(N-methyl-N-cyclohexylamino)

phenyl]-17α-[3-(2'-tetrahydropyranyloxy)-1-propinyl]-9(10)-estrene(XVI).

IR: (KBr)cm$^{-1}$: 3420 ($C_5$, $C_{17}$—OH), 1610, 1510 ($C_{17}$ one), 840, 808(aromatic hydrogen).

$^1$HNMR: (CDCl$_3$) δ ppm: 0.52(3H, S, $C_{13}$—CH$_3$), 2.72 (3H, S, N—CH$_3$), 3.92(4H, m,—O—CH$_2$CH$_2$—O—), 6.65–7.00(4H, ArH).

(3) Preparation of 11β-[4-(N-methyl-N-cyclohexylamino)phenyl]-17α-(3-hydroxy-1-propinyl)-17β-hydroxy-4,9-estradiene-3-One (XVII)

methyl-N-cyclohexylamino)phenyl]-17α-(3-hydroxy-1-propinyl)-17β-hydroxy-4,9-estradiene-3-one (XVII).

IR: (KBr)cm$^{-1}$: 3400 ($C_{17}$—OH, C≡C—CH$_2$—OH), 1650 (unsaturated one), 1610, 1513(benzene backbone), 865, 810(aromatic hydrogen).

$^1$HNMR: (CDCl$_3$) δ ppm: 0.54(3H, S, $C_{13}$—CH$_3$), 2.72 (3H, m, N—CH$_3$), 5.77(1H, S, $C_4$—H), 6.74–7.10(4H, ArH).

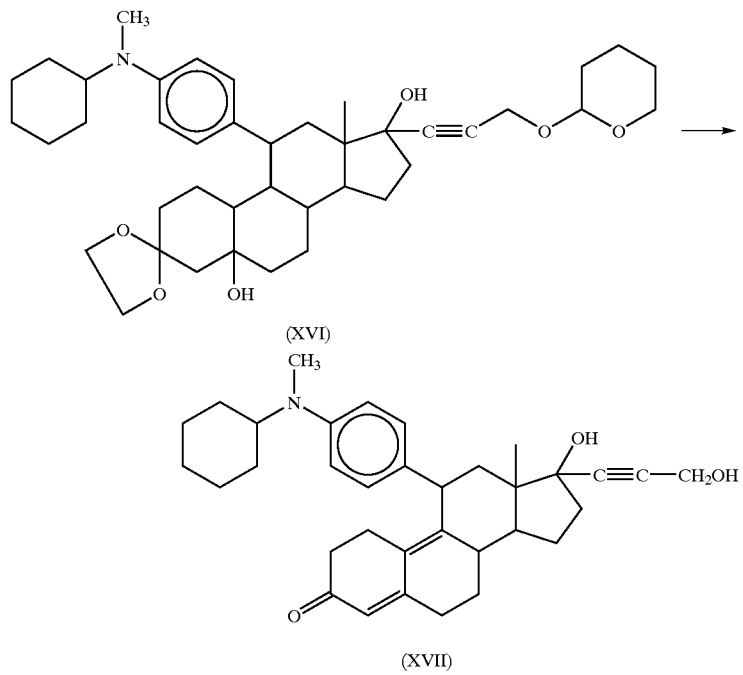

1 g 3,3-ethylenedioxy-5α,17β-dihydroxy-11β-[4-(N-methyl-N-cyclohexylamino)phenyl]-17α-[3-(2'-tetrahydropyranyloxy)-1-propinyl]-9(10)-estrene(XVI) was dissolved in 10 ml 90% ethanol (v/v), 2 ml 30% HCl was added. The mixture was allowed to react for 1 hour while controlling the temperature at 50° C. Diluted ammonia was added to alkalinity. The mixture was extracted with ethyl acetate, dried over anhydrous sodium sulfate and chromatographed on silica gel column to yield 0.5 g 11β-[4-(N-

Example 5

Preparation of 11β-[4-(N-cyclohexylamino)phenyl]-17α-(3-hydroxy-1-propinyl)-17β-hydroxy-4,9-estradiene-3-one (XX)

(1) Preparation of 3,3-ethylenedioxy-5α-hydroxy-11β-[4-(N-cyclohexylamino)phenyl]-9(10)-estrene-17-one(XVIII)

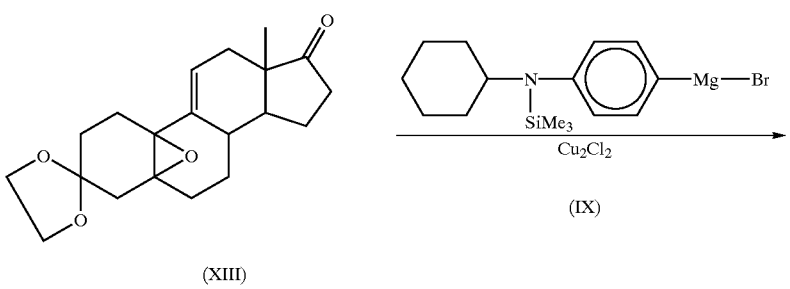

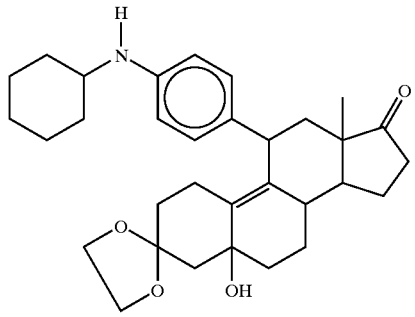

(XVIII)

5 g 3,3-ethylenedioxy-5,10-epoxy-9(11)-estrene-17-one (XIII) was dissolved in 15 ml anhydrows THF. The resulting solution was cooled down to −5° C., to which solution, a catalytic amount of cuprous chloride ($Cu_2Cl_2$) was added. Then 16 ml solution of 4-(N-cyclohexyl-N-trimethylsilylamino)phenyl magnesium bromide (IX) in tetrahydrofuran was added dropwise slowly. After completion of the addition, the mixture was allowed to react for 1 hour at 5° C., and 2 hours at room-temperature and to stand. Saturated ammonium chloride aqueous solution was added and the tetrahydrofuran layer was separated which was washed with saturated saline and dried over anhydrous sodium sulfate. Evaporation of tetrahydrofuran under reduced pressure yielded a residual which was chromatographed on silica gel column to yield 3 g 3,3-ethylenedioxy-5α-hydroxy-11β-[4-(N-cyclohexylamino)phenyl]-9(10)-estrene-17-one(XVIII).

IR: (KBr)$cm^{-1}$: 3420 ($C_5$—OH), 1740 ($C_{17}$ one), 1610, 1510(benzene backbone), 840, 808(aromatic hydrogen).

$^1$HNMR: ($CDCl_3$) δ ppm: 0.52(3H, S, $C_{13}$—$CH_3$), 3.92 (4H, m, —O—$CH_2CH_2$—O—), 4.24(1H, m, $C_{11}$—H), 6.65–7.00(4H, ArH).

(2) Preparation of 3,3-ethylenedioxy-5α,17β-dihydroxy-11β-[4-(N-cyclohexylamino)phenyl]-17α-[3-(2'-tetrahydro pyranyloxy)-1-propinyl]-9 (10)-estrene(XIX)

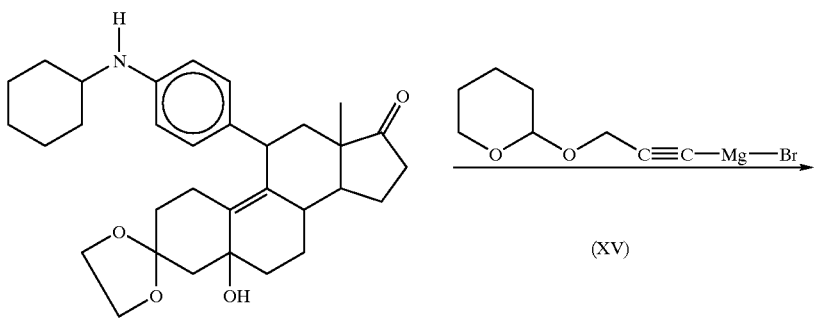

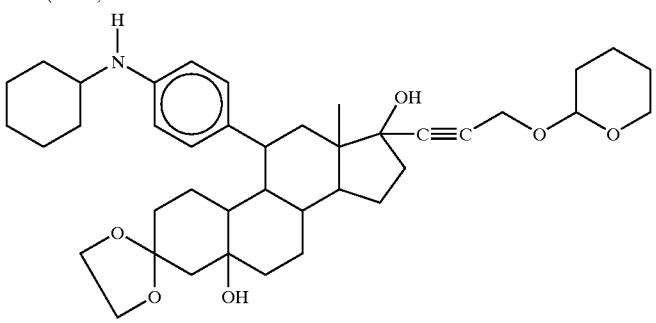

(XIX)

2 g 3,3-ethylenedioxy-5α-hydroxy-11β-[4-(N-cyclohexylamino)phenyl]-9(10)-estrene-17-one(XVIII) dissolved in 14 ml anhydrous tetrahydrofuran (THF) was added dropwise into 36 ml of 0.6 ml/l 3-(2'-tetrahydropyranyloxy)-1-propinyl magnesium bromide (XV) in tetrahydrofuran. After completion of addition, the mixture was allowed to react for 2 hours, poured into saturated ammonium chloride solution, extracted with ethyl acetate, dried over anhydrous sodium sulfate, and chromatographed on silica gel column after evaporation of residual liquid of ethyl acetate yield 3,3-ethylenedioxy-5α,17β-dihydroxy-11β-[4-(N-cyclohexylamino)phenyl]-17α-[3-(2'-tetrahydropyranyloxy)-1-propinyl]-9(10)-estrene(XIX). The yield is 72%.

IR: (KBr)cm$^{-1}$: 3420 ($C_5$,$C_{17}$—OH), 1610, 1510(benzene backbone), 840, 808(aromatic hydrogen).

$^1$HNMR: (CDCl$_3$) δ ppm: 0.52(3H, S, $C_{13}$—CH$_3$), 3.92 (4H, m, —O—CH$_2$CH$_2$—O—), 6.65–7.00(4H, ArH).

(3) Preparation of 11β-[4-(N-cyclohexylamino)phenyl]-17α-(3-hydroxy-1-propinyl)-17β-hydroxy-4,9-estradiene-3-one(XX)

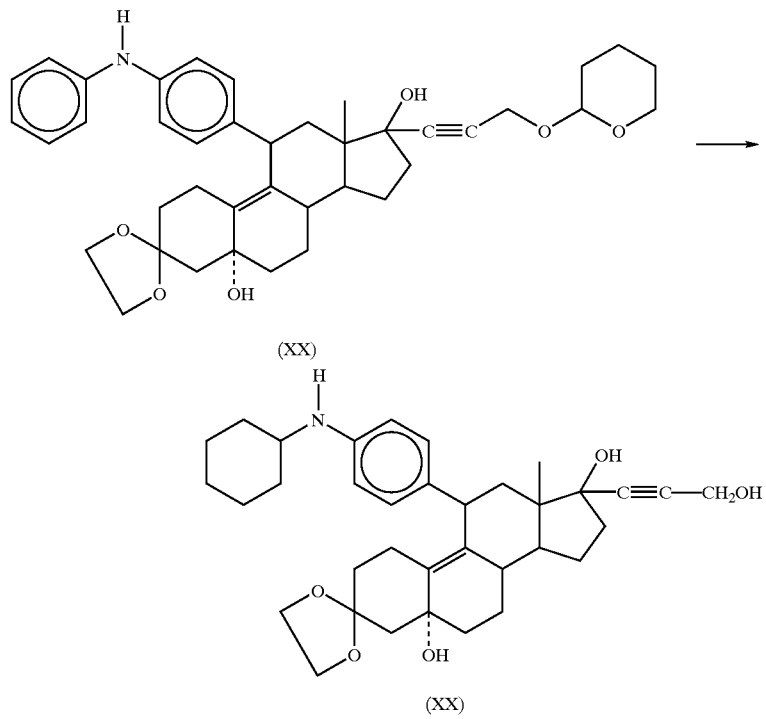

(XX)

3 g 3,3-ethylenedioxy-5α,17β-dihydroxy-11β-[4-(N-cyclohexylamino)phenyl]-17α-[3-(2'-tetrahydropyranyloxy)-1-propinyl]-9(10)-estrene(XIX), 30 ml 90% ethanol (v/v) and 1.5 g PTS were added subsequently into a reaction bulb. The mixtrue was allowed to react for 2 hours in 40° C. Thin layer was used to determine the terminal point. After completion of the reaction, the reaction liquid is poured into 300 ml diluted NaOH aquous solution, extracted with toluene and washed with water to neutral, and recrystallized with methyl acetate after evaparation of the solvent. Then 1.8 g 11β-[4-(N-cyclohexylamino)phenyl]-17α-(3-hydroxy-1-propinyl)-17β-hydroxy-4,9-estradiene-3-one(XX) is prepared.

IR: (KBr)cm$^{-1}$: 3383 ($C_{17}$—OH, —CH$_2$OH), 1647 (unsaturated one), 1613, 1513(benzene backbone), 865, 810 (aromatic hydrogen).

$^1$HNMR: (CDCl$_3$) δ ppm: 0.55(3H, S, C13—CH$_3$), 4.34 (2H, S, —CH$_2$O—), 5.76(1H, S, $C_4$—H), 6.65–6.95(4H, ArH).

Example 6

Preparation of 11β-[4-(N-methyl-N-cycloheptylamino)phenyl]-17α-(1-propinyl)-17β-hydroxy-4,9-estradiene-3-one According to the same method as described in example 1,4-bromo-N-methyl-cyclohexyaniline (II) was replaceed with 4-bromo-N-methyl-N-cycloheptylaniline(XXIII) (see the preparation method in preparation 2). 4-(N-methyl-N-cycloheptylamino)phenyl magnesium bromide is prepared at first. Then the title compound, 11β-[4-(N-methyl-N-cycloheptylamino)phenyl]-17α-(1-propinyl)-17β-hydroxy-4,9-estradiene-3-one is obtained.

IR: (KBr)cm$^{-1}$: 3450 ($C_{17}$—OH), 1660 ($C_3$ one), 1610, 1513(benzene backbone), 860, 810(aromatic hydrogen).

$^1$HNMR: (CDCl$_3$) δ ppm: 0.57(3H, S, $C_{13}$—CH$_3$), 1.88 (3H, S, C≡C—CH$_3$), 2.70 (3H, S, N—CH$_3$), 5.72(1H, S, $C_4$—H), 6.66–6.99(4H, ArH).

Example 7

Preparation of 11β-[4-(N-cycloheptylamino)phenyl]-17α-(1-propinyl)-17β-hydroxy-4,9-estradiene-3-one According to the same method as described in example 2,4-bromo-N-cyclohexylaniline (VII) was replaced with 4-bromo-N-cycloheptylaniline(XXV) (see the preparation method in preparation 3). 4-(N-cycloheptyl-N-trimethylsilylamino)phenyl magnesium bromide is prepared at first. Then the title compound, 11β-[4-(N-cycloheptylamino)phenyl]-17α-(1-propinyl)-17β-hydroxy-4,9-estradiene-3-one is obtained.

IR: (KBr)cm$^{-1}$: 3400 ($C_{17}$—OH), 1660 (unsaturated one), 1612, 1508(benzene backbone), 860, 803(aromatic hydrogen).

$^1$HNMR: (CDCl$_3$) δ ppm: 0.55(3H, S, $C_{13}$—CH$_3$), 1.87 (3H, S, C≡C—CH$_3$), 4.4 (1H, S,$C_{11}$—H), 5.8(1H, S, $C_4$—H), 6.8–7.20(4H, ArH).

Example 8

Preparation of 2-methylol-11β-[4-(N-methyl-N-cycloheptylamino)phenyl]-17α-(1-propinyl)-17β-hydroxy-4,9-estradiene-3one According to the same method as example 3, 11β-[4-(N-methyl-N-cyclohexylamino)phenyl]-17α-(1-propinyl)-17β- hydroxy-4,9-estradiene-3-one(VI) was replaced with 11β-[4-(N-methyl-N-cycloheptylamino)phenyl]-17α-(1-propinyl)-17β-hydroxy-4,9-estradiene-3-one. Then the title compound, 2-methylol-11β-[4-(N-methyl-N-cycloheptylamino)phenyl]-17α-(1-propinyl)-17β-hydroxy-4,9-estradiene-3-one is obtained.

IR: (KBr)cm$^{-1}$: 3400 ($C_{17}$—OH, =C—OH), 1650 (unsaturated One), 1605, 1506(benzene backbone), 870, 815(aromatic hydrogen).

$^1$HNMR: (CDCl$_3$) δ ppm: 1.00(3H, S, C13—CH$_3$), 1.8 (3H, S, C≡C—CH$_3$), 2.83 (3H, S, N—CH$_3$), 6.70–7.0(4H, ArH).

Example 9

Preparation of 11β-[4-(N-methyl-N-cycloheptylamino)phenyl]-17α-(3-hydroxy-1-propinyl)-17β-hydroxy-4,9-estradiene-3-one According to the same method as described in example 4,4-(N-methyl-N-cyclohexylamino)phenyl magnesium bromide (III) was replaced with 4-(N-methyl-N-cycloheptylamino)phenyl magnesium bromide. Then the title compound, 11β-[4-(N-methyl-N-cycloheptylamino)phenyl]-17α-(3-hydroxy-1-propinyl)-17β-hydroxy-4,9-estradiene-3-one is obtained.

IR: (KBr)cm$^{-1}$: 3400 ($C_{17}$—OH, C≡C—CH$_2$—OH), 1650 (unsaturated One), 1608, 1500 (benzene backbone), 860, 815(aromatic hydrogen).

$^1$HNMR: (CDCl$_3$) δ ppm: 0.52 (3H, S, $C_{13}$—CH$_3$), 2.70 (3H, S, N—CH$_3$), 5.75 (1H, S, $C_4$—H), 6.6–7.0(4H, ArH).

Example 10

Preparation of 11β-[4-(N-cycloheptylamino)phenyl]-17α-(3-hydroxy-1-propinyl)-17β-hydroxy-4,9-estradiene-3-one According to the same method as described in example 5,4-(N-cyclohexyl-N-trimethylsilylamino)phenyl magnesium bromide (IX) was replaced with 4-(N-cycloheptyl-N-trimethylsilylamino)phenyl magnesium bromide. Then the title compound, 11β-[4-(N-cycloheptylamino)phenyl]-17α-(3-hydroxy-1-propinyl)-17β-hydroxy-4,9-estradiene-3-one is obtained.

IR: (KBr)cm$^{-1}$: 3418 ($C_5$, $C_{17}$—OH), 1660 ($C_3$ One), 1615, 1501 (benzene backbone), 841, 805(ArH).

$^1$HNMR: (CDCl$_3$) δ ppm: 0.51 (3H, S, $C_{13}$—CH$_3$), 4.32 (2H, S, —CH$_3$O—), 5.70 (1H, S, $C_4$—H), 6.6–7.1(4H, ArH).

The inventor found that the compound of form (VI) had good effects on treating diseases related to progestin dependence, controlling fertility, abortion or contraception and anticancer. Compared with Mifepristone, the compound of form (VI) had better effects on killing tumor cell, inhibiting rat's mammary cancer induced by MNU and anti-early pregnancy, anti-implanation of rat.

The specific pharmaceutical experiments are as following:

Example 11

The effect of the compound of formula (VI) in killing tumor cells

Procedures

Human mammary cancer cells (MCF-7, T47D, commercially available) were prepared as 1×10$^4$/ml cell suspension in RPMI 1640 medium containing 10% calf serum and used to inoculate a 96-well plate at 100 μl/well. The plate was incubated for 24 hours in an incubator in 5% CO$_2$ at 37° C. Two experimental groups each receiving compound of formula (VI) or Mifepristone (commercially available) (triplicate well/group each receiving 100 μl RPMI 1640 medium containing various concentrations of drug) and a control group (each well receiving RPMI medium containing equal volume of solvent) were incubated for 4–6 days in an incubator in 5% CO$_2$ at 37° C. The cultural supernatant was discarded and 0.04% 100 μl MTT prepared with RPMI 1640 was added into each well. Incubation was carried out at 37° C. for 4 hours. The supernatant was discarded and 150 μl dimethyl sulfoxide was added into each well to dissolve Fomazan particles. After being shaked slightly, OD value was measured using a Model 550 Enzyme Labelling Equipment at a wavelength of 540 nm. The rate of inhibition of cells was graphed against the various concentrations of the drug to produce a dosage response curve from which 50% inhibiting concentration IC$_{50}$ was derived.

Experimental Results

As can be seen from Table 1, the compound of formula (VI) has significant inhibition effect on human mammary cancer (MCF-7, T47D) which is stronger than that of Mifepristone.

TABLE 1

The effect of compound of formula (VI) in killing tumor cells

| Groups | IC$_{50}$ (×10$^{-5}$ mol/L) | |
|---|---|---|
| | compound of formula (VI) | Mifepristone |
| MCF-7 | 0.55 ± 0.072 | 1.08 ± 0.810 |
| T 47 D | 0.64 ± 0.315 | 1.10 ± 0.903 |

Example 12

The inhibiting effect of the compound of formula (VI) on MNU-induced rat mammary cancer Procedures Sprague-Dawley rats which are 5–7 weeks old and weighing 90–120 g were treated with an amount of carcinogenic chemical (MNU, commercially available) to induce rat mammary cancer and were divided into a group with cancer-induction alone, a group with mifepristone and two treatment groups with the compound of formula (VI). Each group except for the group with cancer-induction alone was endogastrically administrated with corresponding dose one time per day. After 30 days, the animals were sacrificed by decapitation. Indices such as body weight and tumor weight of each group of the animals were compared. The mean value of the groups was calculated and the rate of tumor growth inhibition derived. Rate of tumor inhibition %=(mean value of the group with cancer-induction alone–mean value of the treatment group)/mean value of the group with cancer-induction alone×100%

Experimental Results

As can be seen from Table 2, the compound of formula (VI) has significant inhibition effect on MNU-induced rat mammary cancer and has better inhibiting effect on cancer at a lower dose than that of Mifepristone group.

TABLE 2

Comparison of rate of inhibition ratio of the compound of formula (VI) and Mifepristone on MNU-induced rat mammary cancer

| Groups | Dosage (mg/kg) | Inhibition (%) |
|---|---|---|
| Compound of Formula (VI) | 10 | 50.4 |
|  | 20 | 89.3 |
| Mifepristone | 40 | 72.1 |

Example 13

The effect of the compound of formula (VI) in stopping early pregnancy

Procedures

Both sexes of Sprague-Dawley rats were placed into a cage and were allowed to copulate. Those animals which were found to carry spermatozoa in vagina on the next day was considered as gravidity $d_1$. Pregnant rats were randomly divided into 11 groups of 10. The control group was administrated with 0.5% CMC-Na solution. 6 Groups were administered with the compound of formula (VI) at doses of 2.0, 1.6, 1.28, 1.02, 0.82 and 0.66 mg/kg respecticely. 4 Groups were administered with Mifepristone at doses of 3.5, 2.45, 1.72 and 1.2 mg/kg respectively. The groups were administered endogastrically once a day (dose 2 ml/kg) for 3 consecutive days starting from gravidity $d_7$. Animals in which ecolporrhagia was not detected and no signs of embryo implantation were found on dissection examination were considered as not pregnant and were not counted. The animals were sacrificed and laparotomized on gradivity $d_{14}$ and the numbers of living embryos, dead embryos, implantation sites and yellow bodies in the uterus were counted. The number of the pregnant animals were counted and compared with that of the control group. $ED_{50}$ of the two test drugs and its credibility interval was calculated with Bliss's method.

Experimental Results

The compound of formula (VI) at 2 mg/kg/day has a complete early pregnancy-stopping effect on rats of gradivity $d_{7-9}$ with $ED_{50}$ being 1.1439±0.1590 (0.9959–1.3139) mg/kg. Mifepristone at 3.5 mg/kg also has a complete early pregnancy-stopping effect but with $ED_{50}$ being 2.123±0.4468 (1.7227–2.6164) mg/kg. It is obvious that the early pregnancy-stopping effect of the compound of formula (VI) is stronger than that of Mifepristone.

Example 14

Test of the compound of formula (VI) on its anti-implantation effect in rat

Procedures

Both sexes of Sprague-Dawley rats were placed into a cage and were allowed to copulate. Those animals which were found to carry spermatozoa in vagina on the next day was considered as gravidity $d_1$. Pregnant rats were randomly divided into 10 groups of 10. The control group was administered with 0.5% CMC-Na solution. 5 Groups were administered with the compound of formula (VI) and 4 groups were administered with Mifepristone. The groups were administered endogastrically once a day for 4 consecutive days starting from gravidity $d_1$. The groups of animals were laparotomized on gravidity $d_{14}$ and their uterus examined. The number of pregnant animals was counted. $ED_{50}$ of the two drugs was calculated with Bliss's method.

Experimental Results

The anti-implantation $ED_{50}$ of the compound of formula (VI) in gravidity $d_{1-4}$ rats was 2.3409±0.6191 mg/kg, while that of Mifepristone was 6.6855±1.5523 mg/kg. It is obvious that the compound of formula (VI) has a stronger anti-implantation effect than that of Mifepristone.

Example 15

The composition and preparation of tablets

| The composition of per 1000 tablets is as follows: | |
|---|---|
| The compound of formula (VI) | 25 g |
| Polyvinylpyrrolidone | 2 g |
| Lactose | 12 g |
| Starch | 10 g |
| Microcyrstalline cellulose | 6 g |
| Polyethylene glycole 6000 | 8 g |
| Colloidal silica | 0.2 g |
| Magnesium stearate | 0.8 g |
| Total amount | 64 g |

The compound of formula (VI) was ground to certain fineness and uniformly screened together with polyvinylpyrrolidone, lactose, starch, microcrystalline cellulose and polyethylene glycol 6000. Appropriate quantity of 50% ethanol was added. Pelletization was carried out according to conventional technique. Dried particles were pressed to produce tablets after adding colloidal silica and magnesium stearate.

Example 16

The composition and preparation of sustained release tablets The composition of per 1000 tablets is as follows:

| The compound of formula (VI) | 25 g |
|---|---|
| Hydroxypropylmethylcellulose | 15 g |
| Lactose | 50 g |
| Carbopol | 5 g |
| Sodium lauryl sulfate | 0.5 g |
| Polyethylene glycol 6000 | 5 g |
| Magnesium stearate | 1 g |
| Total amount | 101.5 g |

The compound of form (VI) was ground to certain fineness and was uniformly screened together with hydroxypropylmethylcellulose, lactose, carbopol, sodium lauryl sulfate and polyethylene glycol 6000. Appropriate quantity of 95% ethanol was added. Pelletization was carried out according to conventional technique. Dried particles were pressed to produce tablets after adding magnesium stearate.

Example 17

The composition and preparation of drop pills

| The composition of per 1000 drop pills | |
|---|---|
| The compound of formula (VI) | 10 g |
| Polyethylene glycol 8000 | 60 g |
| Stearic acid | 3 g |
| Total amount | 73 g |

Polyethylene glycol 8000 was uniformly mixed with stearic acid. The mixture was heated (80–90° C.) while stirring until completely melted. Compound of formula (VI) ground to certain fineness was added. After stirring to homogenous solution the temperature was kept at 70–80° C. Drop pills were produced according to conventional technique.

Example 18

The composition and preparation of suspension

| The composition of per 100 ml suspension | |
|---|---|
| The compound of formula (XVII) | 0.25 g |
| Tween 80 | 1 g |
| Sodium carboxymethylcellulose | 0.5 g |
| Colloidal silica | 0.5 g |
| Glycerine | 2 g |
| Distilled water | to 100 ml |
| Total amount | 100 ml |

Compound of formula (XVII) was ground to certain fineness and sodium carboxymethylcellulose solution, Tween 80, colloidal silica and glycerine were added. A suspension was produced according to copnventional technique after treatment with colloid mill.

What is claimed is:

1. A compound according to formula (I),

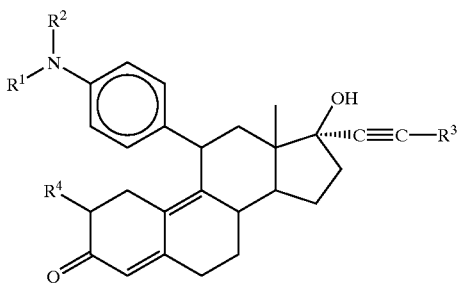

(I)

wherein $R^1$ is cyclohexyl -or cycloheptyl, $R^2$ is hydrogen or C1-C6 alkyl, $R^3$ is hydrogen or C1-C6 alkyl or methylol, $R^4$ is hydrogen or hydroxymethylene with the proviso that when $R^1$ is cyclohexyl, $R^3$ is methyl, and $R^4$ is hydrogen, $R^2$ is not ethyl, and a pharmaceutical acceptable salt thereof.

2. A compound according to claim 1, wherein $R^2$ is hydrogen or methyl, $R^3$ is methyl or methylol, and a pharmaceutically acceptable salt thereof.

3. A compound according to claim 1 which is 11β-[4-(N-methyl-N-cyclohexylamino)phenyl]-17α-(1-propinyl)-17β-hydroxy-4,9-estradiene-3-one and a pharmaceutically acceptable salt thereof.

4. A compound according to claim 1 which is 11β-[4-(N-cyclohexylamino)phenyl]-17α-(1-propinyl)-17β-hydroxy-4,9-estradiene-3-one and a pharmaceutically acceptable salt thereof.

5. A compound according to claim 1 which is 2-hydroxymethylene-11β-[4-(N-methyl-N-cyclohexylamino)phenyl]-17α-(1-propinyl)-17β-hydroxy-4,9-estradiene-3-one and a pharmaceutically acceptable salt thereof.

6. A compound according to claim 1 which is 11β-[4-(N-methyl-N-cyclohexylamino)phenyl]-17α-(3-hydroxy-1-propinyl)-17β-hydroxy-4,9-estradiene-3-one and a pharmaceutically acceptable salt thereof.

7. A compound according to claim 1 which is 11β-[4-(N-cyclohexylamino)phenyl]-17α-(3-hydroxy-1-propinyl)-17β-hydroxy-4,9-estradiene-3-one and a pharmaceutically acceptable salt thereof.

8. A compound according to claim 1 which is 11β-[4-(N-methyl-N-cycloheptylamino)phenyl]-17α-(1-propinyl)-17β-hydroxy-4,9-estradiene-3-one and a pharmaceutically acceptable salt thereof.

9. A compound according to claim 1 which is 11β-[4-(N-cycloheptylamino)phenyl]-17α-(1-propinyl)-17β-hydroxy-4,9-estradiene-3-one and a pharmaceutically acceptable salt thereof.

10. A compound according to claim 1 which is 2-hydroxymethylene-11β-[4-(N-methyl-N-cycloheptylamino)phenyl]-17α-(1-propinyl)-17β-hydroxy-4,9-estradiene-3-one and a pharmaceutically acceptable salt thereof.

11. A compound according to claim 1 which is 11β-[4-(N-methyl-N-cycloheptylamino)phenyl]-17α-(3-hydroxy-1-propinyl)-17β-hydroxy-4,9-estradiene-3-one and a pharmaceutically acceptable salt thereof.

12. A compound according to claim 1 which is 11β-[4-(N-cycloheptylamino)phenyl]-17α-(3-hydroxy-1-propinyl)-17β-hydroxy-4,9-estradiene-3-one and a pharmaceutically acceptable salt thereof.

13. A method for preparation of 11β-[4-(N-methyl-N-cyclohexylamino)phenyl]-17α-(1-propinyl)-17β-hydroxy-4,9-estradiene-3-one and a pharmaceutically acceptable salt thereof, which comprises the following steps:

(1) preparation of Grignard reagent (III)

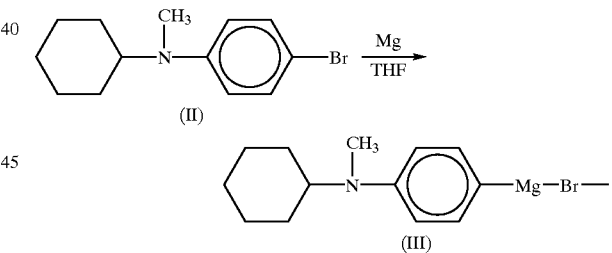

wherein 4-bromo-N-methyl-N-cyclohexylaniline (II) is reacted with magnesium in tetrahydrofuran (THF) to obtain Grignard reagent of formula (III);

(2) $C_{11}$ additive reaction

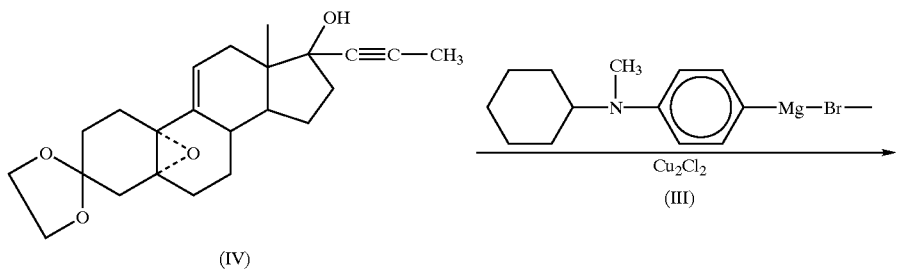

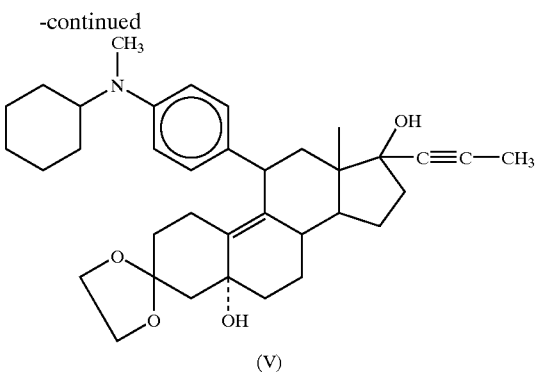

(V)

wherein compound of formula (IV) and the Grignard reagent of formula (III) prepared in step (1) are brought to an additive reaction to obtain compound of formula (V); and (3) hydrolytic reaction

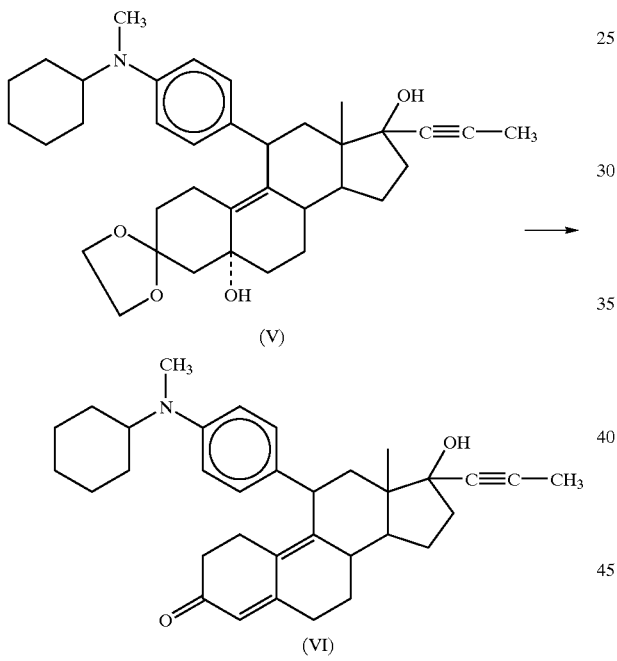

wherein the compound of formula (V) prepared in step (2) is subjected to a Hydrolytic reaction to obtain compound of form (VI).

14. A method for preparation of 11β-[4-(N-cyclohexylamino)phenyl]-17α-(1-propinyl)-17β-hydroxy-4,9-estradiene-3-one and a pharmaceutically acceptable salt thereof, which comprises the following steps:

(1) preparation of Grignard reagent of formula (IX)

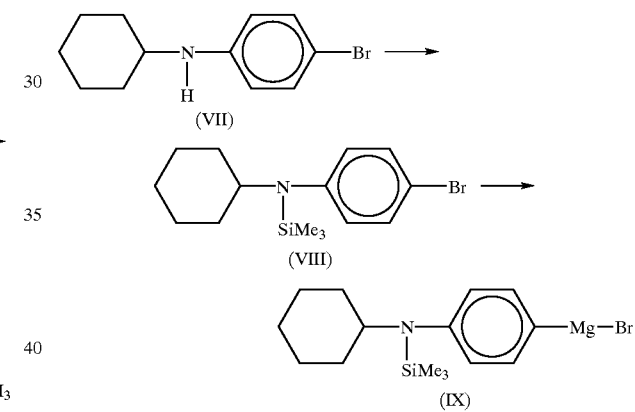

wherein 4-bromo-N-cyclohexylaniline (VII) is first protected by trimethylchlorosilane, then reacted with magnesium in THF to obtain Grignard reagent of formula (IX);

(2) $C_{11}$ additive reaction

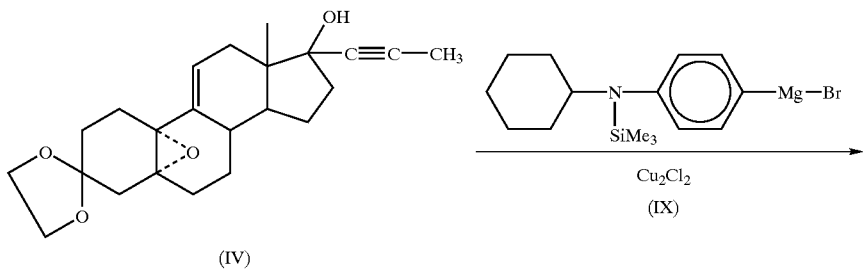

-continued

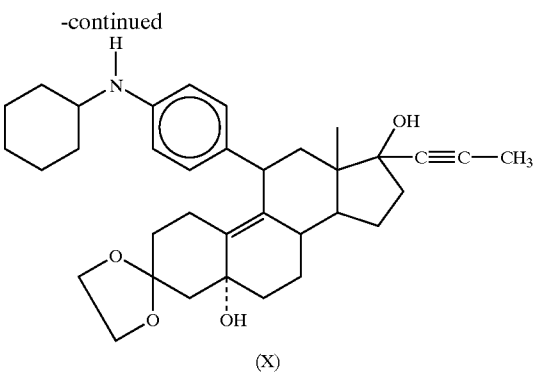

(X)

wherein compound of formula (IV) and the Grignard reagent of formula (IX) prepared in step (1) are brought to an additive reaction to obtain compound of formula (X); and (3) hydrolytic reaction

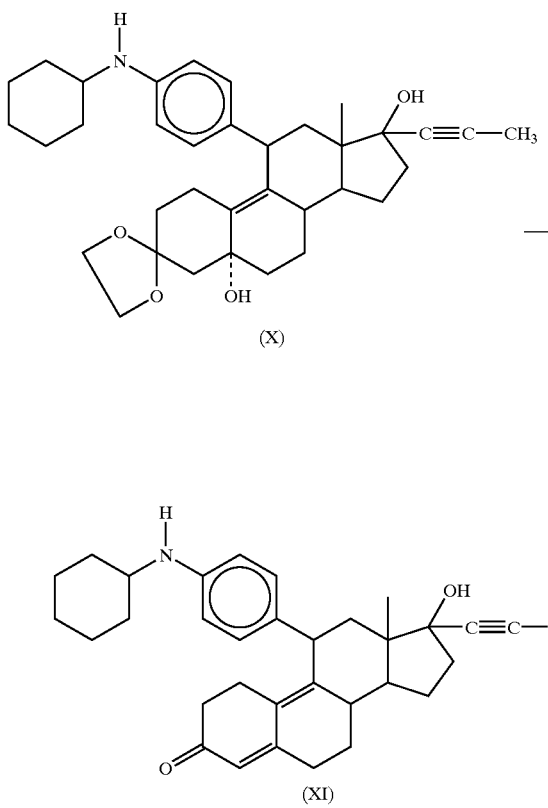

wherein the compound of formula (X) prepared in step (2) is subjected to a hydrolytic reaction to obtain compound of formula (XI).

15. A method for preparation of 2-hydroxymethylene-11β-[4-(N-methyl-N-cyclohexylamino)phenyl]-17α-(1-propinyl)-17β-hydroxy-4,9-estradiene-3-one and a pharmaceutically acceptable salt thereof, which comprises a formylation reaction

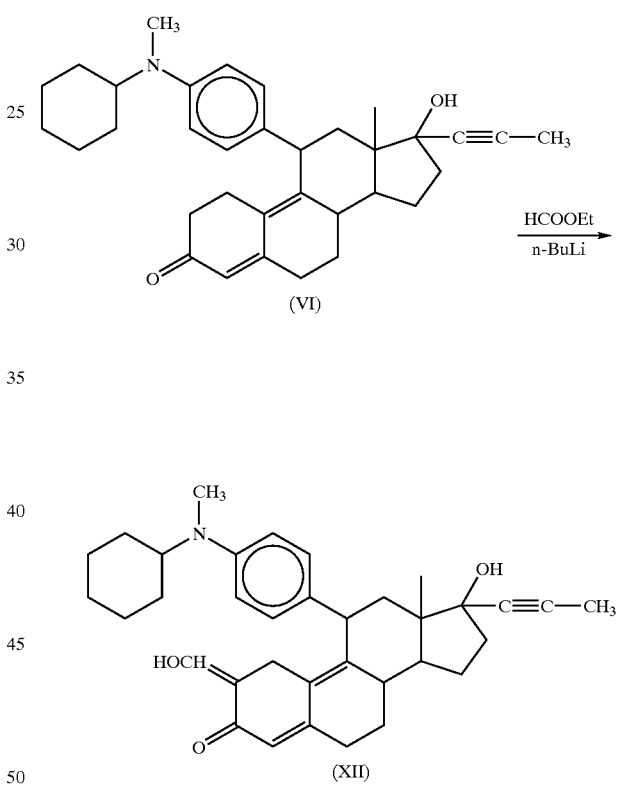

wherein compound of formula (VI) prepared in step (3) of claim 13 is subjected to a formylation reaction to obtain compound of formula (XII).

16. A method for preparation of 11β-[4-(N-methyl-N-cyclohexylamino)phenyl]-17α-(3-hydroxy-1-propinyl)-17β-hydroxy-4,9-estradiene-3-one and a pharmaceutically acceptable salt thereof, which comprises the following steps:

(1) $C_{11}$ additive reaction

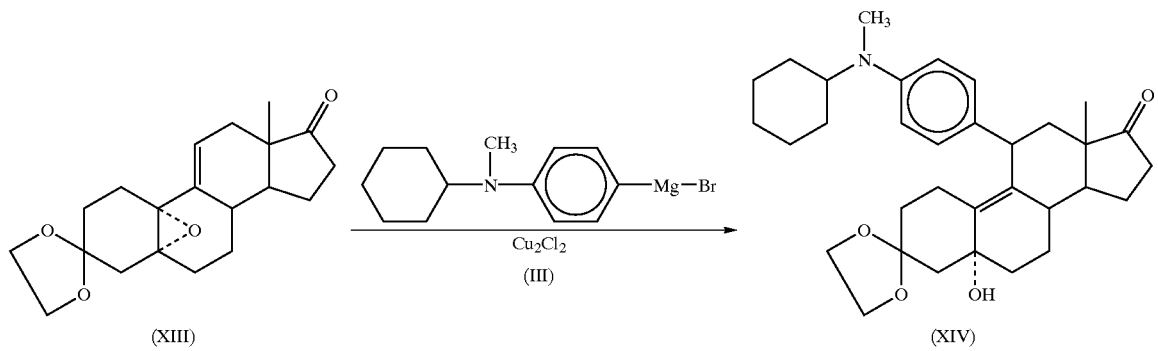

wherein compound of formula (XIII) and the Grignard reagent of formula (III) prepared in step (1) of claim 13 are brought to an additive reaction to obtain compound of formula (XIV);

(2) $C_{17}$ additive reaction

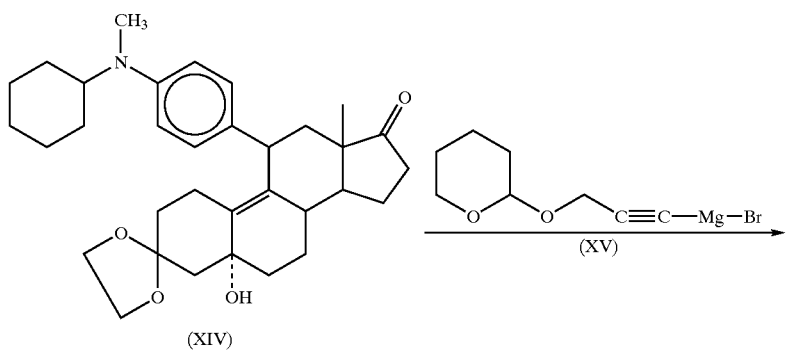

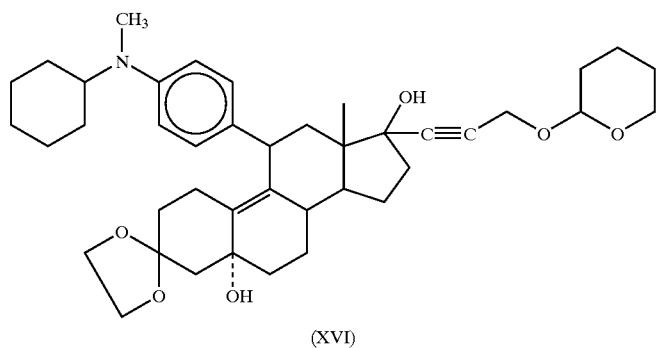

wherein compound of formula (XIV) prepared in step (1) and Grignard reagent of formula (XV) are brought to an additive reaction to obtain compound of fomula (XVI); and (3) hydrolytic reaction

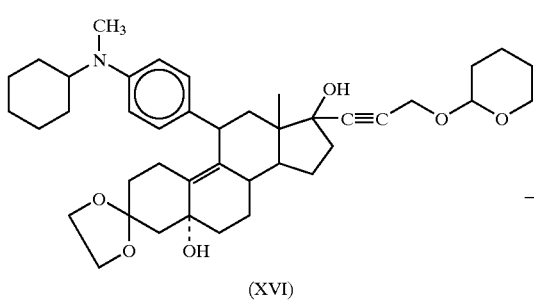

(XVI)

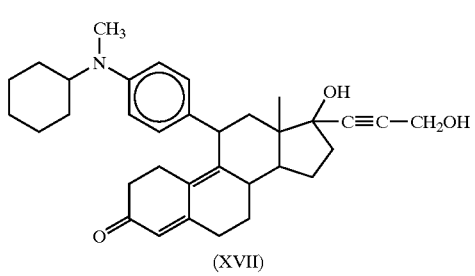

(XVII)

wherein the compound of formula (XVI) prepared in step (2) is subjected to a hydrolytic reaction to obtain compound of formula (XVII).

17. A method for preparation of 11β-[4-(N-cyclohexylamino)phenyl]-17α-(3-hydroxy-1-propinyl)-17β-hydroxy-4,9-estradiene-3-one and a pharmaceutically acceptable salt thereof, which comprises the following steps:

(1) C$_{11}$ additive reaction

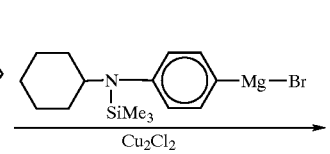

(XIII) (IX)

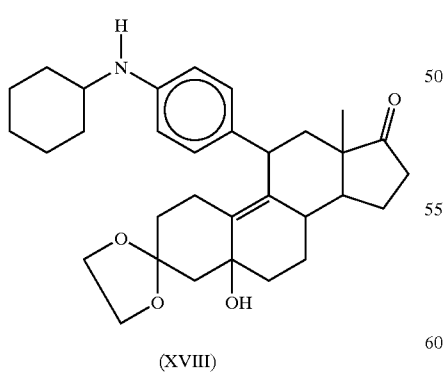

(XVIII)

wherein compound of formula (XIII) and Grignard reagent of formula (IX) prepared in step (1) of claim 14 are brought to an additive reaction to obtain compound of formula (XVIII);

(2) C$_{17}$ additive reaction

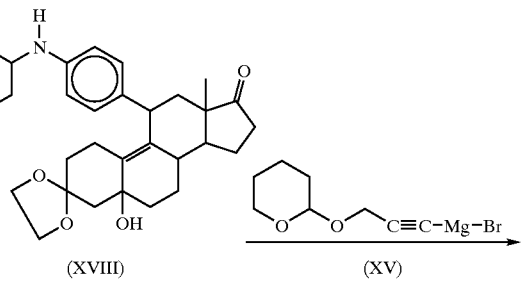

(XVIII) (XV)

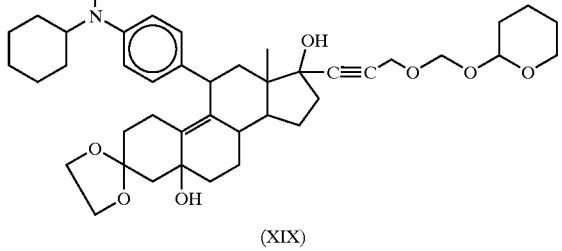

(XIX)

wherein compound of formula (XVIII) prepared in step (1) and Grignard reagent of formula (XV) are brought to an additive reaction to obtain compound of formula (XIX); and (3) hydrolytic reaction

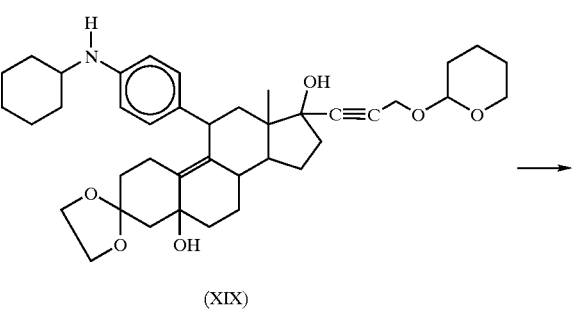

(XIX)

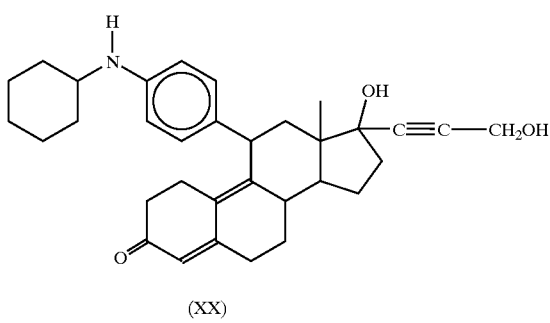

(XX)

wherein compound of formula (XIX) prepared in step (2) is subjected to a hydrolytic reaction to obtain compound of formula (XX).

18. A pharmaceutical composition for treating diseases associated with progestin dependence, which comprises a therapeutically effective amount of the compound of claim 1 and a pharmaceutically acceptable carrier or an auxiliary.

19. A pharmaceutical composition for controlling fertility which comprises a therapeutically effective amount of the compound of claim 1 and a pharmaceutically acceptable carrier or auxiliary.

20. A pharmaceutical composition for abortion or contraception which comprises a therapeutically effective amount of the compound of claim 1 and a pharmaceutically acceptable carrier or auxiliary.

21. A pharmaceutical composition for controlling neoplasm which comprises a therapeutically effective amount of the compound of claim 1 and a pharmaceutically acceptable carrier or auxiliary.

22. A method for treating diseases associated with progestin dependence, which comprises administering a composition comprising a therapeutically effective amount of the compound of claim 1 to a subject.

23. A method for controlling fertility, which comprises administering a composition comprising a therapeutically effective amount of the compound of claim 1 to a subject.

24. A method for inducing abortion associated with progestin dependence, which comprises administering a composition comprising a therapeutically effective amount of the compound of claim 1 to a subject.

25. A method for treating cancers associated with progestin dependence, which comprises administering a composition comprising a therapeutically effective amount of the compound of claim 1 to a subject.

* * * * *

UNITED STATES PATENT AND TRADEMARK OFFICE
CERTIFICATE OF CORRECTION

PATENT NO.    : 6,514,956 B1                                             Page 1 of 1
DATED         : February 4, 2003
INVENTOR(S)   : Lianzhi Chen et al.

It is certified that error appears in the above-identified patent and that said Letters Patent is hereby corrected as shown below:

<u>Title page,</u>
Item [75], Inventors, replace "Wenliung Chen" with -- Wenliang Chen --.
Item [73], Assignee, insert -- Siniwest Holdings, Inc. (US) --.

Signed and Sealed this

Fourth Day of November, 2003

JAMES E. ROGAN
*Director of the United States Patent and Trademark Office*